US009451923B2

(12) United States Patent
Hemmendorff et al.

(10) Patent No.: US 9,451,923 B2
(45) Date of Patent: Sep. 27, 2016

(54) ADAPTING A SCAN MOTION IN AN X-RAY IMAGING APPARATUS

(75) Inventors: Magnus Hemmendorff, Tullinge (SE); Torbjorn Hjarn, Vaxholm (SE); Mats Lundqvist, Taby (SE); Jonas Rehn, Sollentuna (SE)

(73) Assignee: Koninklijke Philips N.V., Eindhoven (NL)

( * ) Notice: Subject to any disclaimer, the term of this patent is extended or adjusted under 35 U.S.C. 154(b) by 113 days.

(21) Appl. No.: 14/126,646

(22) PCT Filed: Jun. 27, 2012

(86) PCT No.: PCT/EP2012/062487
§ 371 (c)(1),
(2), (4) Date: Jan. 28, 2014

(87) PCT Pub. No.: WO2013/004572
PCT Pub. Date: Jan. 10, 2013

(65) Prior Publication Data
US 2014/0198896 A1  Jul. 17, 2014

Related U.S. Application Data

(60) Provisional application No. 61/504,259, filed on Jul. 4, 2011.

(30) Foreign Application Priority Data

Jul. 4, 2011  (SE) ...................................... 1150625

(51) Int. Cl.
*A61B 6/00* (2006.01)
*A61B 6/02* (2006.01)

(52) U.S. Cl.
CPC ............. *A61B 6/4452* (2013.01); *A61B 6/025* (2013.01); *A61B 6/027* (2013.01); *A61B 6/502* (2013.01); *A61B 6/547* (2013.01)

(58) Field of Classification Search
USPC ............ 378/91, 95, 101, 145, 193, 204, 205
See application file for complete search history.

(56) References Cited

U.S. PATENT DOCUMENTS

| 4,115,698 A | 9/1978 | Hounsfield |
| 6,496,557 B2 | 12/2002 | Wilson et al. |
| 7,123,683 B2 | 10/2006 | Osamu |
| 7,123,684 B2 | 10/2006 | Jine et al. |
| 7,302,031 B2 | 11/2007 | Hjarn et al. |

(Continued)

FOREIGN PATENT DOCUMENTS

| FR | 2657771 A1 | 8/1991 |
| JP | 2005230536 A | 9/2005 |

(Continued)

*Primary Examiner* — Nicole Ippolito

(57) ABSTRACT

According to one embodiment, the x-ray apparatus comprises an x-ray source adapted to emit an x-ray beam, a detector adapted to receive the x-ray beam of the x-ray source, wherein the x-ray source is adapted to be moved in relation to a first portion of the x-ray apparatus, wherein the detector is adapted to be moved in relation to a first portion of the x-ray apparatus, the x-ray apparatus further comprising a control unit for controlling the movement of the x-ray source and detector, wherein the x-ray source and the detector are adapted to rotate in relation to a first portion of the x-ray apparatus, wherein further the x-ray beam is directed essentially towards the detector during the movement of the x-ray source and the detector.

43 Claims, 16 Drawing Sheets

(56) References Cited

U.S. PATENT DOCUMENTS

| | | |
|---|---|---|
| 7,453,979 B2 | 11/2008 | Tomonari |
| 2007/0230660 A1* | 10/2007 | Herrmann ............... A61N 5/10 378/65 |
| 2010/0091940 A1 | 4/2010 | Ludwig et al. |
| 2010/0260316 A1 | 10/2010 | Stein et al. |

FOREIGN PATENT DOCUMENTS

| | | |
|---|---|---|
| WO | 9849939 A1 | 11/1998 |
| WO | 03037046 A2 | 5/2003 |
| WO | 03073939 A1 | 9/2003 |
| WO | 2005077277 A1 | 8/2005 |

\* cited by examiner

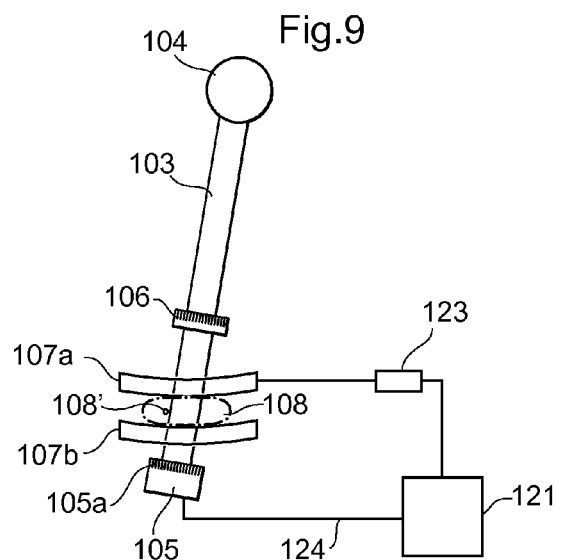
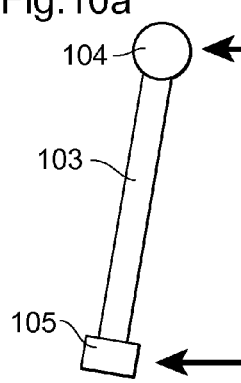
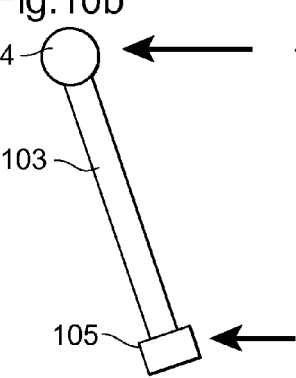
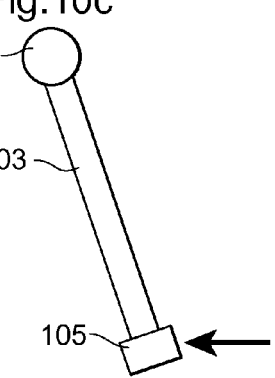
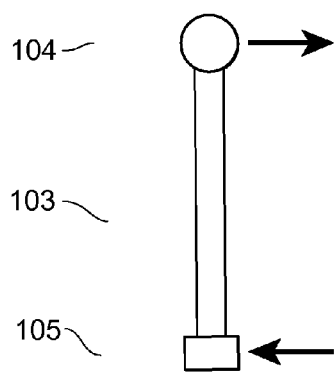
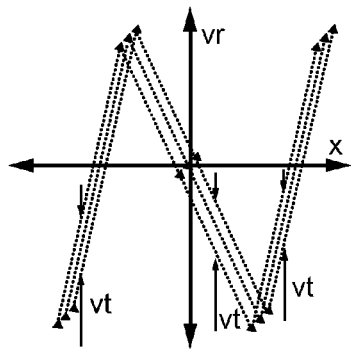

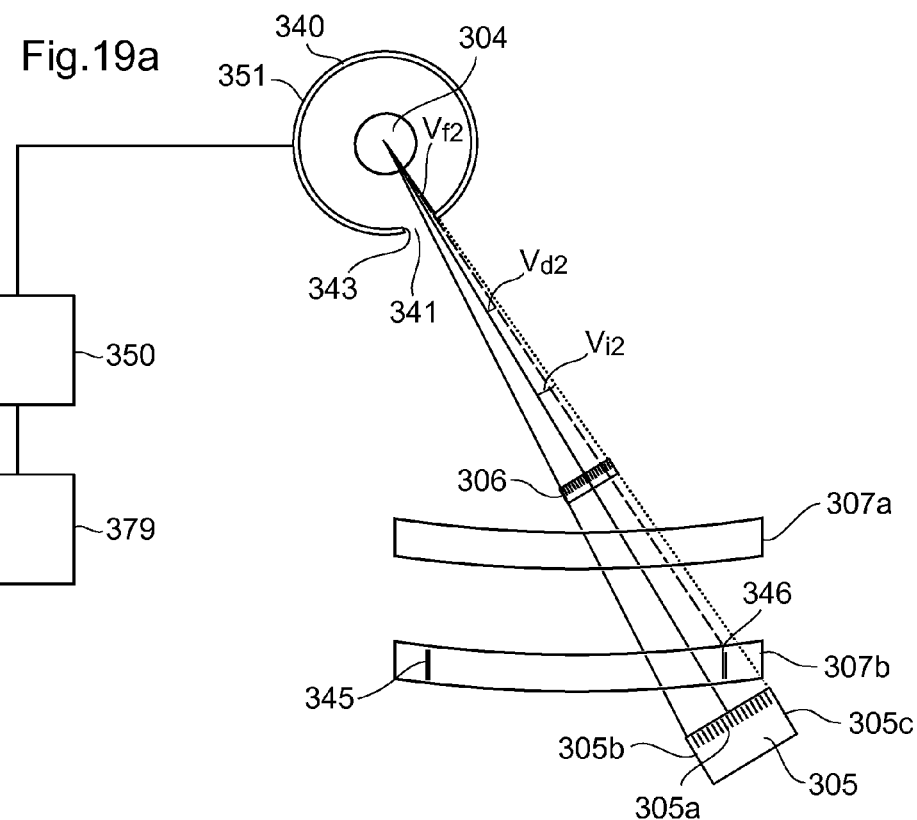
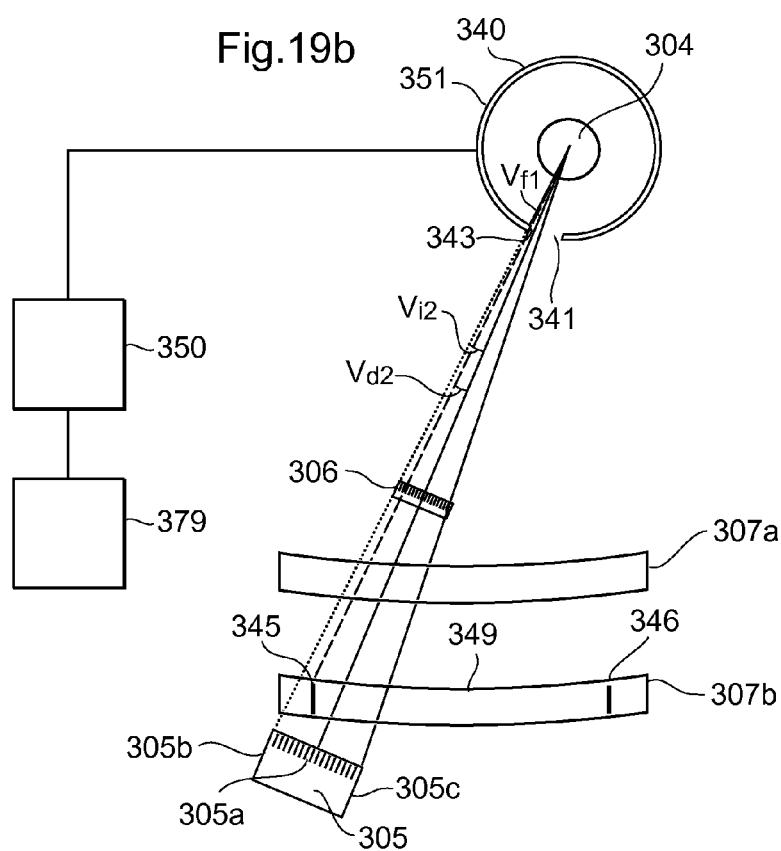

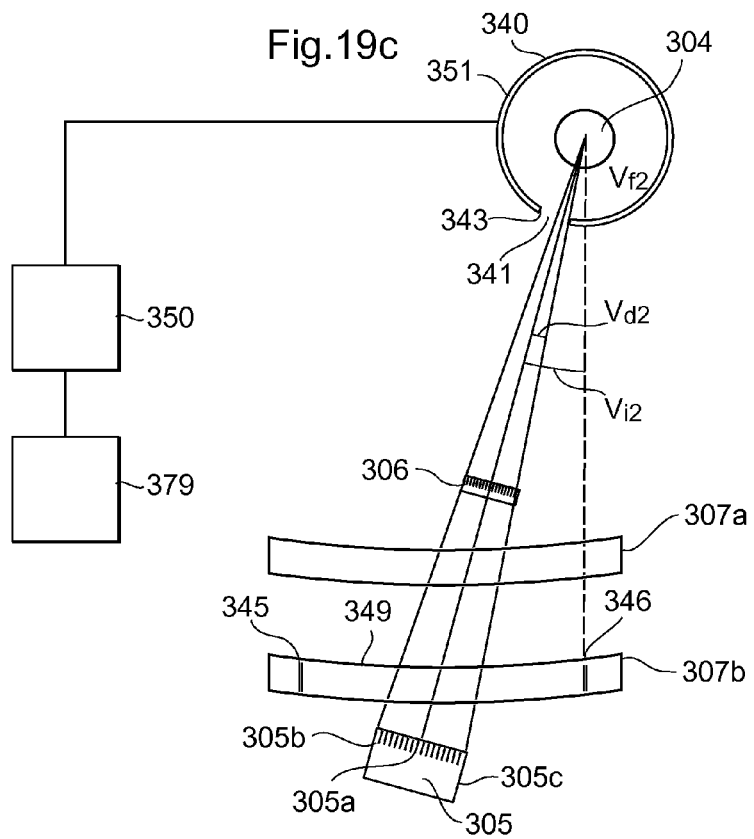
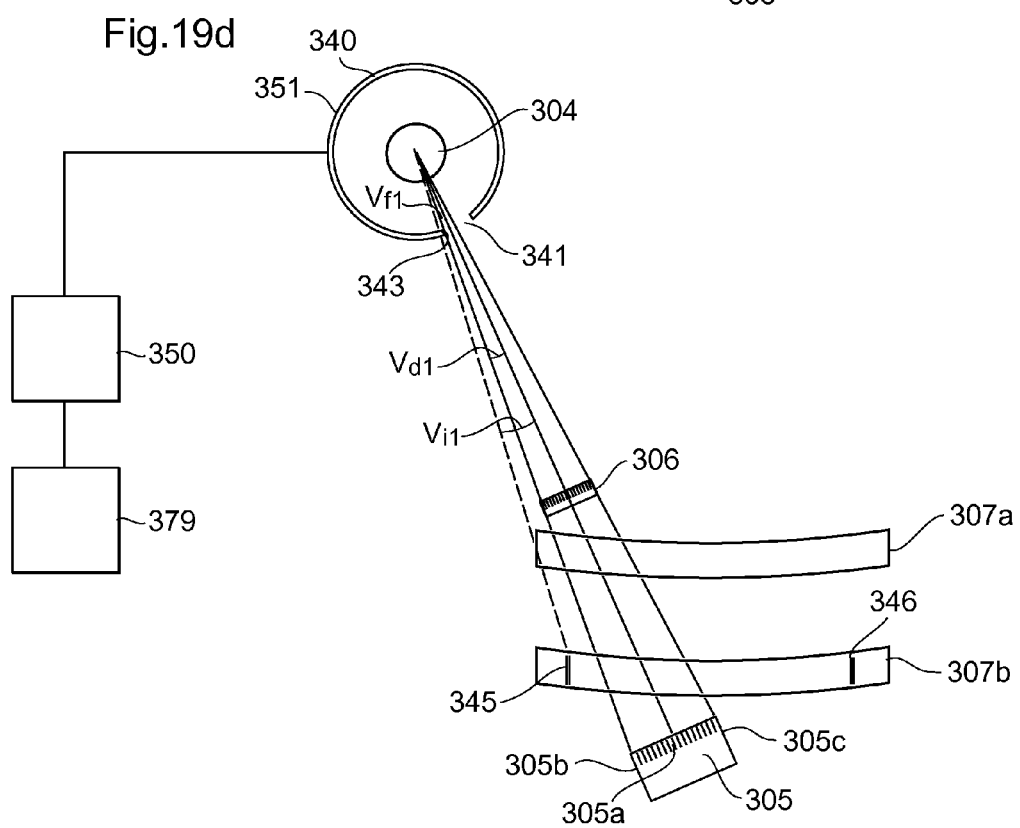

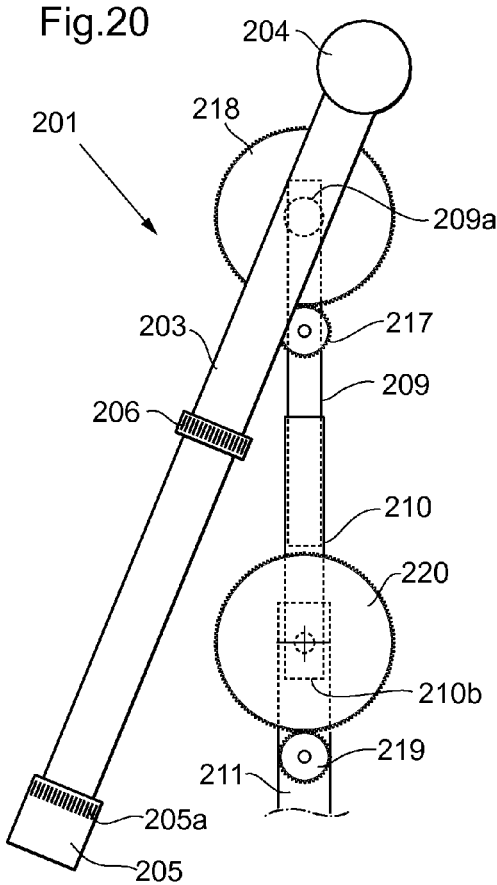
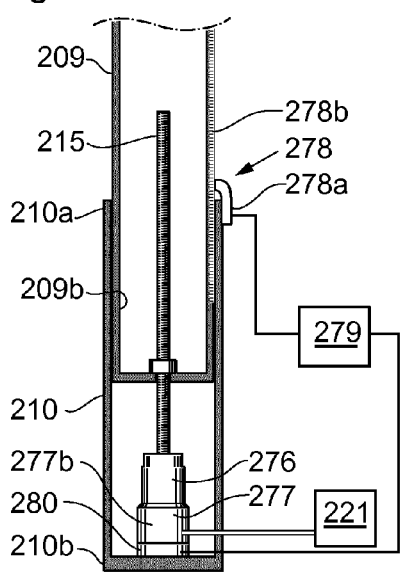
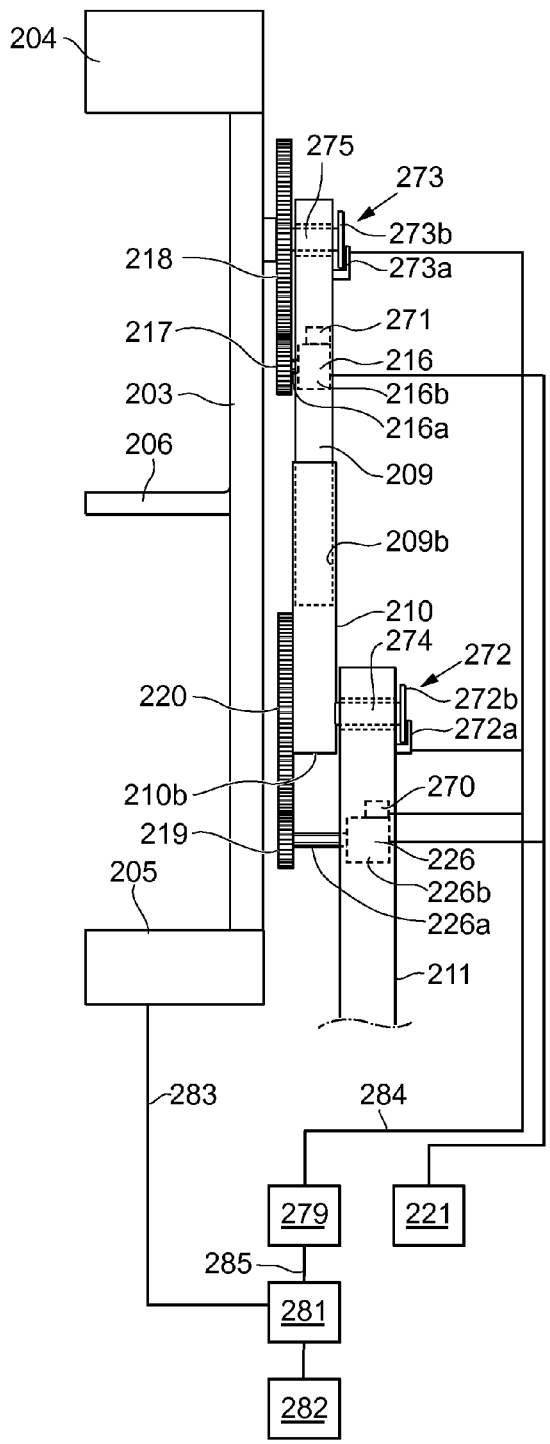

ADAPTING A SCAN MOTION IN AN X-RAY IMAGING APPARATUS

CROSS-REFERENCE TO PRIOR APPLICATIONS

This application is the U.S. National Phase application under 35 U.S.C. §371 of International Application No. PCT/EP2012/062487, filed on Jun. 27, 2012, which claims the benefit of U.S. Provisional Patent Application No. 61/504,259, filed on Jul. 4, 2011 and Application No. 1150625-0 (SE), filed on Jul. 4, 2011. These applications are hereby incorporated by reference in their entirety herein.

TECHNICAL FIELD

The present invention relates generally to an x-ray imaging apparatus in the field of mammography, tomosynthesis and radiography.

BACKGROUND ART

Tomosynthesis is used to reconstruct a three-dimensional image of a person's body part, for example a breast in a mammography examination. The typical arrangement for creating such images require that the focal spot of an x-ray source (104, 204, 304) is allowed to rotate in relation to an object (108, 208, 308) such as a breast, whereby an interval of projection angles through each location in the object (108, 208, 308) is scanned creating individual projection images for each projection angle. With data comprising a multitude of 2D projection images, reconstruction into a 3D image is possible using computers running algorithms including back-projection as a computational step. Examples of algorithms are filtered back projection, algebraic reconstruction and Lange-Fessler Convex algorithm from 1995. Examples x-ray imaging apparatuses enabling the construction of tomosynthesis images are for instance U.S. Pat. No. 7,302,031 and U.S. Pat. No. 6,496,557.

In prior art, x-ray systems with the capability of creating projection angles, i.e. tomo-angles, has been proposed. Generally, such solutions allow either a linear or rotational movement of the x-ray source (104, 204, 304) in relation to the detector (105, 205, 305) and the object (108, 208, 308) to be scanned, wherein the detector (105, 205, 305) may also be adapted to be movable in a linear or rotational manner. It has been proposed to allow for the creation of both 2D images, wherein the x-ray source (104, 204, 304) is stationary and the detector (105, 205, 305) rotates around the x-ray source (104, 204, 304) and the investigated object, and 3D tomosynthesis images, wherein the x-ray source (104, 204, 304) is movable in relation to the detector (105, 205, 305) and the investigated object, in the same system. Examples of such systems can for instance be found in U.S. Pat. No. 7,302,031 and U.S. Pat. No. 6,496,557.

X-ray systems as described in the prior art with the capacity to generate variable tomosynthesis images requires heavier systems and preferably more complex scan motions with more degrees of freedom than traditional 2D x-ray imaging systems in order to achieve the sought after projection angles and images. However, the scan movement during a mammography investigation of such systems is set by an operator based on preset movement schemes. This will have a negative implication on the image quality as the most optimal projection angles are not achieved for each object (108, 208, 308) that is scanned, concerning for instance the size, thickness and other characteristics of the object. Further, such systems does not have the ability to prevent certain scan movements that should be avoided based on characteristics of the object that is scanned in a direct or indirect manner.

Further, the solutions in the prior art does not describe an adaptive controlling of the scan movement wherein external data is taken into account in order to optimize the tomo-angles during a scan of an object.

In prior art shielding apparatuses used in mammography applications it has been proposed to use box or telescopic shielding means for protecting the patient and operator against scatter. Such exemplary prior art can for instance be seen in EP1480560 B1 which discloses scanning apparatus wherein the x-ray source is fixed during the scanning movement. The shielding means herein is automatically installed in a vertical direction based upon the installment of the patient breast support which height is based on the size of the object to be scanned. The purpose of such solutions are to prevent scattered radiation, not to prevent the direct radiation that does not add to the generation or improvement of an image of a scanned object.

In prior art it has been proposed to use a position encoder in an x-ray imaging system to synchronize the receiver readout with the scanning motion so as to yield a high fidelity composite 2D image. Herein the encoders are used to produce signals as a function of detector array motion, wherein these signals are used to trigger charge shifting across an array of pixels. Since the charge shifting is referenced to encoder output, synchronization is maintained despite variances in drive speed or due to other irregularities.

In other prior art documents, tomosynthesis is a method used to reconstruct a three-dimensional image of a person's body part, for example a breast in a mammography examination. The typical arrangement for creating such images requires that the focal spot of an x-ray source is allowed to move in relation to an object such as a breast, whereby an interval of projection angles through each location in the object is scanned creating individual projection images for each projection angle. With data comprising a multitude of 2-dimensional projection images, reconstruction into a 3D image is possible using computers running reconstruction algorithms involving so-called back-projection as a computational step. Examples of documents disclosing x-ray imaging apparatuses enabling the construction of tomosynthesis images are for instance U.S. Pat. No. 7,302,031 and U.S. Pat. No. 6,496,557.

Tomosynthesis scanners with variable scan motions require heavier systems and preferably more complex scan motions with more degrees of freedom than traditional x-ray imaging systems in order to achieve and optimize the projection angles and images. However, the reconstruction of 3D images requires a precision in the scan motion in order not to cause motion blur in the reconstructed image which is non-compliant to the heavy systems described in which play is prone to develop over time, for instance in various actuation mechanisms that are used for controlling the movement of a certain scan, as well as due to the motors controlling the scan motion which are not possible to control in a perfect manner. In order to obtain precise image quality without artifacts resembling motion blur, prior art may have to rely on expensive movement control systems and motors, and force transmission without backlash or deflection.

SUMMARY OF INVENTION

An object of the present invention is to alleviate some of the disadvantages of the prior art and to provide an improved device for an x-ray imaging system wherein scan motion is optimized based on external data.

According to one embodiment, the x-ray apparatus comprises an x-ray source adapted to emit an x-ray beam, a detector adapted to receive the x-ray beam of the x-ray source, wherein the x-ray source is adapted to be moved in relation to a first portion of the x-ray apparatus, wherein the detector is adapted to be moved in relation to a first portion of the x-ray apparatus, the x-ray apparatus further comprising a control unit for controlling the movement of the x-ray source and detector, wherein the x-ray source and the detector are adapted to rotate in relation to a first portion of the x-ray apparatus, wherein further the x-ray beam is directed essentially towards the detector during the movement of the x-ray source and the detector, wherein the control unit is adapted to receive external data, wherein the control unit is further adapted to control the movement of the x-ray source and the detector based on external data, wherein the x-ray apparatus further comprises at least one position adjustable compression paddle, and a means for determining the position of the at least one compression paddle adapted to output paddle position data corresponding to the position of the at least one compression paddle, and wherein the external data, which is received by the control unit, comprises paddle position data.

According to another embodiment, the detector is adapted to sense characteristics of an x-ray beam in real time during a scan movement, wherein the detector is further adapted to output x-ray beam data corresponding to characteristics of the x-ray beam, and wherein the external data, which is received by the control unit for controlling the remainder of the scan movement of the x-ray source and the detector, comprises x-ray beam data.

According to another embodiment, the detector is adapted to receive impinging photons from the x-ray source during a scan movement, the detector further being adapted to detect an x-ray intensity based on the rate of impinging photons, wherein the control unit is further adapted to receive external data from the detector that a scan of an object placed in the x-ray beam is initiated by detecting a lower intensity, as an object to be scanned starts attenuating photons from the x-ray beam.

According to another embodiment, the control unit is adapted to control a scan movement and/or the remainder of a scan movement of the x-ray source and the detector based on the external data, such that a tomosynthetic scan movement is performed, wherein tomographic projection angles of an object placed in the x-ray beam are optimized based on the external data.

According to another embodiment, the control unit is adapted to control the movement of x-ray source and the detector such that the speed of at least the x-ray source decreases as the first end of the detector senses a decreased count rate at least during the scan of the object.

According to another embodiment, a first detected x-ray intensity decreases the speed of at least the x-ray source to a first velocity, a second detected x-ray intensity decreases the speed of the x-ray source to a second velocity, wherein, if the first detected x-ray intensity is lower than the second detected x-ray intensity, the first velocity is lower than the second velocity at least during a scan of the object.

According to another embodiment, the control unit is adapted to control the speed of the detector such that the velocity of the detector is lower than the speed of the x-ray source at least during a scan of an object.

According to another embodiment, the control unit is adapted to control the speed of the x-ray source and the detector such that a ratio between the velocity of the x-ray source and the detector is lower for a lower lower detected x-ray intensity compared to a higher detected x-ray intensity during a scan of the object and/or compared between two separate scan of objects.

According to another embodiment, the control unit is adapted to control the speed of the x-ray source and the detector such that the ratio is high enough to allow the x-ray source to pass the detector in a horizontal direction during the movement of the x-ray source and the detector, wherein the count rate corresponds to the object being scanned.

According to another embodiment, the control unit is adapted to control the speed of at least the x-ray source based on the position of the at least one compression paddle during a scan of the object such that a first position of the at least one compression paddle sets the speed of at least the x-ray source to a first velocity, a second position of the at least one compression paddle sets the speed of at least the x-ray source to a second velocity, wherein, if the first position of the at least one compression paddle is higher in a vertical direction than the second position of the at least one compression paddle, the first velocity is lower than the second velocity.

According to another embodiment, the control unit is adapted to control the speed of the x-ray source and the detector such that a ratio between the velocity of the x-ray source and the detector is lower for a higher position of the compression paddle compared to a lower position of the compression paddle at least during a scan of the object.

According to another embodiment, the control unit is adapted to control the speed of the x-ray source and the detector such that the ratio is high enough to allow the x-ray source to pass the detector in a horizontal direction at least during a scan of the object.

According to another embodiment, the control unit is adapted to control the movement of the x-ray source and the detector such that a straight line between the x-ray source and a centre of the detector in relation to a vertical line essentially extending through a first portion of the x-ray apparatus defines an angle ($\alpha$) wherein the detector moves before the x-ray source towards the object to be scanned, wherein the angle ($\alpha$) is set during a start of a movement of the x-ray source and the detector until scan of an object is initiated, wherein the angle ($\alpha$) decreases with the position of the at least one compression paddle.

According to another embodiment, the control unit is adapted to control the speed of the x-ray source and the detector such that the ratio there between is high enough so that the angle ($\alpha$) has a first value, passes 0 degrees and has a second value at the end of the scan of an object, wherein the first and second values essentially maximized under constraint of avoiding collision with a compression paddle.

According to another embodiment, the control unit is adapted to control the angle ($\alpha$) such that the spread of local tomographic projection angles remains constant during the entire scan movement.

According to another embodiment, the control unit is adapted to control the movement of the x-ray source and the detector such that the angle ($\alpha$) does not exceed a limit value, wherein the limit value is continuously varying with the position of the x-ray source and the positions of the detector, and furthermore depends on the position and type of the compression paddle.

According to another embodiment, the limit value of angle ($\alpha$) depends on the position of the at least one compression paddle.

According to another embodiment, the apparatus comprises two compression paddles, wherein an object can be compressed between said two compression paddles, wherein the limit value of angle ($\alpha$) decreases if the distance between the compression paddles increases.

According to another embodiment, the x-ray apparatus further comprises a scan arm, wherein the x-ray source is arranged at a first position on the scan arm and the detector is arranged at a second position on the scan arm.

According to another embodiment, the first position of the scan arm corresponds to a first end of the scan arm and the second position of the scan arm corresponds to a second end of the scan arm.

According to another embodiment, the scan arm further comprises a multi-slit collimator arranged between the x-ray source and the detector on the scan arm, wherein the control unit is adapted to control the movement of the x-ray source and the detector such that a collision between the at least on compression paddle and the collimator is prevented.

According to another embodiment, the control unit is adapted to change direction of the x-ray source and/or the detector at a first turning point for the x-ray source and at a first turning point for the detector respectively, wherein the x-ray source either moves in a second direction or stops after reaching the first turning point and the detector either moves in a second direction or stops after reaching the first turning point, and wherein the second directions are essentially opposite the first directions before reaching the first turning points.

According to another embodiment, the control unit is further adapted to select the number of turning points, zero or more, and their positions depending on said external data.

According to another embodiment, the control unit is further adapted to minimize the number of turning points under the constraint of achieving tomo-angles in the object scan, depending on said external data.

According to another embodiment, the control unit is adapted to control the movement of the x-ray source and the detector such that when both the x-ray source and the detector move towards their first turning points the x-ray source reaches the first turning point before the detector reaches the first turning point.

According to another embodiment, the control unit is adapted to control the movement of the x-ray source and the detector such that the x-ray source and the detector changes direction immediately after reaching the first turning point and starts to move in a second direction.

According to another embodiment, the control unit is adapted to change direction of the x-ray source at a second turning point, wherein the control unit is adapted to control the movement of the x-ray source and the detector such that the x-ray source changes direction and starts to move in a first direction at the second turning point when the detector reaches the first turning point.

According to another embodiment, the x-ray stops after reaching the first turning point until the other of the x-ray source and detector reaches the first turning point, whereafter the x-ray source or starts to move in a second direction.

According to another embodiment, the x-ray source moves with a higher speed than the detector.

According to another embodiment, the control unit is further adapted to control the movement of the x-ray source and the detector based on a positions of the x-ray source and the detector.

According to another embodiment, the positions are predefined.

According to another embodiment, the control unit is adapted to control the movement of the x-ray source and the detector such that the speed of the x-ray source is higher than the speed of the detector.

According to another embodiment, the predefined positions corresponds to positions reached during a scan of an object, whereby an area in the object has been identified that requires a specific scan movement, wherein the ratio of the speed of the x-ray source and the detector increases.

According to another embodiment, an optimization is performed for maximizing a tomographic angle within a detected object, under a tradeoff of minimizing the movement of the X-ray source.

According to another embodiment, that the speed of at least the x-ray source decreases as the predefined position of the x-ray source is reached, and the predefined position of the detector is reached.

According to another embodiment, the x-ray apparatus further comprises a device for taking biopsy samples from a breast as the positions are reached, wherein the positions corresponds to positions whereby an area in the object is identified that requires biopsy sampling.

According to another embodiment, the x-ray apparatus comprises an upper portion and a lower portion, wherein the x-ray source is pivotally arranged in a first end of a first suspension arm, wherein the second end of a first suspension arm being slidingly arranged in a first end of a second suspension arm, wherein a second end of the second suspension arm is pivotally arranged in a lower portion, wherein a first linear screw is arranged in the x-ray portion near the x-ray source to control the movement of the x-ray source in a horizontal direction, a second linear screw is arranged in the lower portion near the detector assembly to control the movement of the detector assembly in a horizontal direction, and a third linear screw is arranged in the second suspension arm to control the movement of the scan arm in a vertical direction.

According to another embodiment, the first portion of the x-ray apparatus is essentially fixed in space.

According to another embodiment, an x-ray apparatus comprises an x-ray source adapted to emit an x-ray beam, a detector adapted to receive the x-ray beam of the x-ray source, wherein the x-ray source is set up to be moved, wherein the detector is set up to be moved, the x-ray apparatus further comprising a control unit for controlling the movement of the x-ray source and detector, wherein further the x-ray beam is directed essentially towards the detector during the movement of the x-ray source and the detector, wherein the control unit is adapted receive external data, wherein the to control unit is further adapted to control the path of movement of the combination of the x-ray source and the detector based on said external data wherein external data comprises data related to an object.

According to another embodiment, the control unit is adapted to control the movement of the x-ray source along a first movement path and control the movement of the detector along a second movement path respectively during a scan movement, based on external data.

According to another embodiment, the external data is received by the control unit during the scan movement.

According to another embodiment, the external data is related to a boundary or thickness of an object to be scanned, or a region of interest, wherein said apparatus comprises means for measuring said external data after positioning the object but before finishing a scan.

According to another embodiment, movement of the x-ray source along a first movement path and the movement of the detector along the second movement path, corresponds to a combined movement path, wherein said combined movement path can be represented by a curve through a multi-dimensional parametric space involving a position along one axis and an angle between said x-ray source and detector.

According to another embodiment, said first movement path and said second movement path is adapted for optimizing local tomographic projection angles and minimizing movements of said x-ray source.

An object of the present invention is to alleviate some of the disadvantages of the prior art and to provide an improved device for shielding x-ray radiation.

According to one embodiment, the x-ray apparatus comprises an x-ray source adapted to emit an x-ray beam, a detector adapted to receive the x-ray beam of the x-ray source, wherein the x-ray source is adapted to be moved in relation to a first portion of the x-ray apparatus, wherein the detector is adapted to be moved in relation to the first portion of the x-ray apparatus, wherein the x-ray source and the detector are adapted to rotate in relation to the first portion of the x-ray apparatus, wherein further the x-ray beam is directed essentially towards the detector during the movement of the x-ray source and the detector, the x-ray apparatus further comprising; a position sensing arrangement adapted for sensing positions corresponding to the positions of the x-ray source and the detector and transmitting the position signals corresponding to the positions of the x-ray source and the detector as sensed by the position sensing arrangement, a field limiting device, comprising a first side portion and a second side portion and an opening between the side portions, wherein the x-ray beam is allowed to pass through the opening but is blocked by the first and second side portions wherein it is absorbed by the first and second side portions, According to another embodiment, at least the first side portion of the field limiting device is adjustably movable in relation to a center line of the x-ray beam, between a first position and second position wherein the first side portion prevents a larger share of the x-ray beam from passing the field limiting device in the second position than in the first position, wherein the apparatus further comprises a first control unit adapted for receiving the position signals from the position sensing arrangement and wherein the first control unit is adapted to control the movement of at least the first side portion based on the position signals.

According to another embodiment, the first side portion prevents a larger share of the x-ray radiation from passing the field limiting device in any position between the first position and the second position compared to the first position.

According to another embodiment, the second position of the first side portion is closer to a center of the x-ray beam than the first position of the first side portion.

According to another embodiment, the x-ray apparatus further comprises an image field having at least a first end and a second end, wherein the first side portion is adapted to move towards a second position to prevent x-ray radiation from irradiating an area outside the first image end, and the second side portion is adapted to move towards a second position to prevent x-ray radiation from irradiating an area outside the second image end.

According to another embodiment, the x-ray apparatus further comprises a scan arm, wherein the x-ray source is arranged on a first position of a scan arm, wherein the detector is arranged on a second position of the scan arm, wherein the field limiting device is arranged on a third position of the scan arm, such that a movement of the x-ray source causes a movement of the field limiting device.

According to another embodiment, an opening of the field limiting device comprises a first angle $v_{f1}$ from the center line of the x-ray beam to the end of the first side portion seen from the x-ray source, a second angle $v_{f2}$ from a center line of the x-ray beam to the end of the second side portion seen from the x-ray source wherein $v_{i2}$ is the angle from a center line of the x-ray beam to the second image end seen from the x-ray source, wherein $v_{i1}$ is the angle from a center line of the x-ray beam to the first image end seen from the x-ray source, wherein $v_{d2}$ is the angle from a center line of the x-ray beam to a second end of the detector seen from the x-ray source, wherein $v_{d1}$ is the angle from a center line of the x-ray beam to a first end of the detector seen from the x-ray source, wherein the first side portion is adapted to move between a first and second position if $v_{i1} < v_{d1}$, such that $v_{f1} \leq v_{i1}$, wherein the second side portion is adapted to move between a first and second position if $v_{i2} < v_{d2}$ such that $v_{f2} \leq v_{i2}$ According to another embodiment, the first side portion is adapted to move between a first and second position if $v_{i1} > v_{d1}$, such that $v_{d1} \leq v_{f1} \leq v_{i1}$ wherein the second side portion is adapted to move between a first and second position if $v_{i2} > v_{d2}$, such that $v_{d2} \leq v_{f2} \leq v_{i2}$.

According to another embodiment, the first side portion moves towards the second position if $v_{i1}$ is decreasing and moves towards the first position if $v_{i1}$ is increasing, and the second side portion moves towards the second position if $v_{i2}$ is decreasing and moves towards the first position if $v_{i2}$ is increasing.

According to another embodiment, wherein the x-ray apparatus is setup to perform plural scan sweeps, the x-ray apparatus further comprises a second control unit for controlling the movement of the x-ray source and the detector, wherein the detector comprises a plurality of detector lines, wherein the first control unit is adapted to calculate the angles of the x-ray beam towards each of the detector lines in relation to a vertical line at predefined positions along a path essentially extending in a horizontal direction, based on the position signals from the position sensing arrangement, wherein first control unit is adapted to save the calculated angles wherein the first control unit is adapted to control at least the first side portion of the field limiting device to prevent the x-ray beam from being received by the detector lines more than once for each calculated angle at each predefined position along the path essentially extending in a horizontal direction.

According to another embodiment, the second control unit is adapted to change direction of the x-ray source and/or the detector at a first turning point of the x-ray source and a first turning point of the detector respectively, wherein the x-ray source and the detector, after reaching the turning point, move in a second direction which is essentially opposite a first direction prior to reaching the turning point, wherein a main scan movement comprises the movement of the x-ray source and the detector before the x-ray source reaches the first turning point and after the detector reaches the first turning point, wherein a bouncing scan movement comprises the movement of the x-ray source and the detector from when r the x-ray source reaches the first turning point until the detector reaches the same turning point or from when the x-ray source reaches the first turning point, the detector reaches the first turning point, and until the x-ray source reaches a second turning point wherein the x-ray source changes direction of movement again, wherein the first control unit is adapted to compare the saved calculated angles during a main scan movement with the calculated angles during a bouncing scan movement, and wherein the first control unit is further adapted to identify and mark the detector lines for which there is an overlap during a main scan and a bouncing scan movement wherein first control unit is adapted to move at least the first side portion towards a second position such that at least the first side portion will essentially cover the marked detector lines from the x-ray beam.

According to another embodiment, the first and second side portions are interconnected with each other.

According to another embodiment, the field limiting device comprises a plate with an aperture.

According to another embodiment, the field limiting device comprises a cylindrical device having an aperture, wherein the portion of the cylindrical device defining a first end of the aperture is the first side portion, and the portion of the cylindrical device defining a second end of the aperture is the second side portion, wherein the cylindrical device is pivotally arranged for rotation around the x-ray source.

According to another embodiment, the cylindrical device is adapted to rotate an angle $v_{rot1}=(v_{f1}-v_{i1})$, if $v_{i1}<v_{f1}$, and wherein the cylindrical device is adapted to rotate an angle $v_{rot2}=(v_{f2}-v_{i2})$, if $v_{i2}<v_{f2}$.

According to another embodiment, the cylindrical device is adapted to rotate an angle $v_{rot1}=(v_{f1}-v_{d1})$, if $v_{i1}>v_{d1}$ and rotate an angle $v_{rot2}=(v_{f2}-v_{d2})$, if $v_{i2}>v_{d2}$.

According to another embodiment, a second side portion is adapted to move towards a first position, a second position or not move, as the first side portion moves towards the second position, wherein the second side portion prevents a larger share of the x-ray beam from passing the field limiting device in a second position than in a first position.

According to another embodiment, the second position of the second side portion is closer to a center line of the field than the first position of the second side portion.

According to another embodiment, the movement of the first and second side portions is performed by an electrical motor, wherein the motor is controlled by the first control unit.

According to another embodiment, the first side portion and second side portion are adapted to slide along at least one linear rail.

According to another embodiment, the first and second side portions are L-shaped.

According to another embodiment, the first side portion and second side portion are made of an x-ray opaque material such as steel and/or lead.

According to another embodiment, the first control unit is adapted to control the movement of a first and second side portion based on the movement of the x-ray source and the movement of the detector.

According to another embodiment, the first control unit is adapted to control the movement of the first and second side portions based on at least one preset scan program.

According to another embodiment, the first position of the scan arm corresponds to a first end of the scan arm, and wherein a second position of the scan arm corresponds to a second end of the scan arm.

According to another embodiment, the first and second control unit is comprised by the same control unit.

According to another embodiment, the path essentially extending in a horizontal direction is located within the distance from an object table to a compression paddle.

According to another embodiment, the first portion of the x-ray apparatus is essentially fixed in space.

According to another embodiment, the x-ray apparatus comprises; an x-ray source (104, 204, 304) adapted to emit an x-ray beam; a detector adapted to receive the x-ray beam of the x-ray source, wherein the x-ray source (104, 204, 304) is adapted to be moved, wherein the detector is adapted to be moved, wherein further the x-ray beam is directed essentially towards the detector during the movement of the x-ray source (104, 204, 304) and the detector, wherein at least the first side portion (140a, 240a, 340a) of the field limiting device (140, 240, 340) is adjustably movable in relation to a center line of the x-ray beam between a first position and second position, wherein the first side portion (140a, 240a, 340a) prevents a larger share of the x-ray beam from passing the field limiting device (140, 240, 340) in the second position than in the first position, wherein the movement of the x-ray source (104, 204, 304) and the detector (105, 205, 305) is synchronized with the movement of the field limiting device (140, 240, 340). With the synchronization, any solution comprising a predefined relationship between the movement of the field limiting device and the movement of the x-ray source and the detector, for instance, the use of predefined movement paths performed at a given time, and during a certain time frame, wherein positions of the x-ray source and the detector are reached at certain points in time, or the use of a stepper motor(s) for driving the movement of the x-ray source and detector.

According to another embodiment, an x-ray apparatus for tomosynthesis imaging comprises an X-ray source, an indicated area for exposure, a detector and a field limiter for controlling an extent of an X-ray beam, a controller for moving in synchronism said field limiter, and said X-ray source during exposure from said X-ray source, said controller being adapted for limiting an edge of said X-ray beam to an edge of said area of exposure.

An object of the present invention is to alleviate some of the disadvantages of the prior art and to provide an improved device for x-ray imaging wherein motion blur in an image reconstruction can be reduced at a low cost.

According to one embodiment, the x-ray apparatus comprises an x-ray source adapted to emit x-ray beams, a detector adapted to receive the x-ray beams emitted by the x-ray source, wherein the x-ray source is arranged to be moved in relation to a first portion of the x-ray apparatus, wherein the detector is arranged to be moved in relation to the first portion of the x-ray apparatus, the x-ray apparatus further comprising a control unit for controlling the movement of the x-ray source and the detector, wherein the x-ray source and the detector are adapted to move in relation to the first portion of the x-ray apparatus, wherein further the x-ray beams are directed essentially towards the detector during the movement of the x-ray source and the detector, wherein data concerning the x-ray beams is read out during the movement of the x-ray source and the detector. According to another embodiment, the x-ray apparatus further comprises a position sensing arrangement adapted for sensing positions corresponding to the positions of the x-ray source and the detector and transmitting the position signals, a recording device adapted to receive and record the position signals corresponding to the positions of the x-ray source and the detector as sensed by the position sensing arrangement, an image reconstruction device connected to the detector via a first connection device, and connected to the recording device via a second connection device, wherein the image reconstruction device is adapted for reconstructing an image based on the recorded positions in the recording device and the read out data from the detector. By including the actual positions of the x-ray source and the detector in the tomosynthesis reconstruction process, the detector readout images can be optimized in terms of reduced motion blur effects.

According to another embodiment, the x-ray apparatus further comprises a scan arm wherein the x-ray source is arranged at a first position of the scan arm and the detector is arranged at a second position of the scan arm.

According to another embodiment, the scan arm is pivotally arranged in a second portion of the x-ray apparatus.

According to another embodiment, the second portion of the x-ray apparatus comprises a first suspension arm wherein the first suspension arm comprises a first and second end and the first end of the scan arm is pivotally arranged in the first end of the first suspension arm.

According to another embodiment, a second end of the first suspension arm is adapted to be linearly displaceable in relation to a first end of a second suspension arm, such that a total length of the first and second suspension arms can be varied.

According to another embodiment, either the second end of the first suspension arm is arranged inside the first end of the second suspension arm or the first end of the second suspension arm is arranged inside the second end of the first suspension arm, wherein the first and second suspension arms have a telescopic relationship.

According to another embodiment, the second end of the second suspension arm is pivotally arranged in a lower portion of the x-ray apparatus.

According to another embodiment, the position sensing arrangement comprises a first position sensing device adapted to sense a relative rotational movement between the scan arm and the second portion of the x-ray apparatus.

According to another embodiment, the first position sensing device comprises a first rotary position encoder arranged essentially where the first end of the scan arm is pivotally arranged in a first end of the first suspension arm.

According to another embodiment, the position sensing arrangement comprises a second position sensing device adapted to sense a relative rotational movement between the second suspension arm and the lower portion of the x-ray apparatus, wherein the second position sensing device comprises a second rotary position encoder.

According to another embodiment, the position sensing arrangement further comprises a third position sensing device adapted to sense the linear displacement between the second end of the first suspension arm and the first end of the second suspension arm.

According to another embodiment, the third position sensing device comprises a position scale arranged either at the second end of the first arm or the first end of the second arm and that the second position sensing device further comprises a position sensor arranged on the other of the second end of the first arm or the first end of the second arm.

According to another embodiment, the x-ray apparatus further comprises a first motor for controlling the rotational movement of the scan arm in relation to a second portion of the x-ray apparatus, wherein the position sensing arrangement comprises a fourth position sensing device adapted to sense the relative rotational position of a casing of the first motor and the rotor of the first motor, wherein the set relative rotational position of the scan arm and the second portion is sensed.

According to another embodiment, the x-ray apparatus further comprises a second motor for controlling the rotational movement of the second portion in relation to the lower portion of the x-ray apparatus, wherein the position sensing arrangement further comprises a fifth position sensing device, adapted to sense the relative rotational position of a casing of the second motor and the rotor of the second motor, wherein the set relative rotational position of the second portion and the lower portion is sensed.

According to another embodiment, the x-ray apparatus further comprises a third motor for controlling the linear displacement of the first end of the first suspension arm in relation to second end of the second suspension arm, wherein in the position sensing arrangement further comprises a sixth position sensing device, adapted to sense the relative rotational position of a casing of the third motor and the rotor of the third motor, whereby the set relative linear displacement of the first end of the first suspension arm in relation to second end of the second suspension arm can be deduced.

According to another embodiment, an alteration of the signals is performed in the image reconstruction device before the reconstruction of an image.

According to another embodiment, the position sensing arrangement is connected to the recording device via a third connection device for transmitting the signals to the recording device, wherein the first, second and third connection devices are one of a signal cable or a transmitter for wireless communication.

According to another embodiment, readout of data is performed upon the position signals from at least one of the fourth, fifth and sixth position sensing devices, corresponding to predefined positions.

According to another embodiment, readout of data is performed at certain predefined points in time.

According to another embodiment, readout of data is performed upon position signals from the position sensing arrangement, corresponding to predefined positions.

According to another embodiment, comprising a method for image reconstruction, the x-ray apparatus comprising an x-ray source and a detector, wherein the x-ray source is adapted to emit x-ray beams, wherein the detector is adapted to receive the emitted x-ray beams, the method including the steps: moving the x-ray source and detector in a linear and/or rotational manner during a scan movement, recording the movement in space of the scan arm at certain predefined positions or at certain points in time, reconstructing an x-ray image based on the recorded movement of the scan arm and the received x-ray radiation.

According to another embodiment, comprising a method for image reconstruction, the movement of the scan arm in space is recorded by recording relative positions of portions of the x-ray apparatus.

According to another embodiment, the x-ray apparatus further comprises a display device adapted to display the generated images, reconstructed by the image reconstruction device.

According to another embodiment, the first portion of the x-ray apparatus is essentially fixed in space.

According to another embodiment, the x-ray source is adapted to be moved in relation to the first portion of the x-ray apparatus along a first movement path, wherein the detector is adapted to be moved in relation to the first portion of the x-ray source along a second movement path, wherein the position sensing arrangement is adapted for sensing the positions of the x-ray source and the detector along the first and second movement paths, respectively.

According to another embodiment, the detector readout and position sensor readouts are performed in synchronism, and said image reconstruction involves adapting coordinates for reconstructed voxels or pixels in the projection image data.

According to another embodiment, the apparatus further comprising a means for synchronization and cross reference of recorded position data and data from said detector, and said means for reconstruction comprises a means for computing coordinates for correspondence between detector data and voxel data.

According to another embodiment, the means for synchronization involves recording timing data corresponding to readouts from detector and/or a position sensor.

According to another embodiment, a scanning apparatus comprising:
scanning mechanics moving with plural degrees of freedom plural position sensors, and a means for recording positions, and an x-ray detector and a means for recording detector readout while scanning,
whereby obtaining a set of projection image data,
a reconstruction means for reconstructing an image volume wherein said reconstruction means is characterized by adapting coordinates using recorded positions.

BRIEF DESCRIPTION OF DRAWINGS

The invention is now described, by way of example, with reference to the accompanying drawings, in which:

FIG. 10a-10d illustrates a schematic view of the scan arm at certain positions of the scan arm during scan movement at a turning point FIG. 10e shows the achieved local tomographic projection angles during the scan movement according to FIG. 10a-10d FIG. 11a-FIG. 11d represents a similar scan movement to that described in FIG. 10a-10d.

FIG. 19a shows the scan arm with a field limiting device according to another embodiment in a first position wherein the detector is outside the image field.

FIG. 19b shows the scan arm with a field limiting device according to another embodiment in a second position wherein the detector is outside the image field.

FIG. 19c shows the scan arm with a field limiting device according to another embodiment in a first position wherein the detector is inside the image field.

FIG. 19d shows the scan arm with a field limiting device according to another embodiment in a second position wherein the detector is inside the image field.

FIG. 20 illustrates a schematic view of an x-ray imaging system

FIG. 21 shows a schematic view of the relationship between the first and second suspension arms FIG. 22 shows a schematic view of a side view of the x-ray apparatus.

DESCRIPTION OF EMBODIMENTS

In the following, a detailed description of the invention is presented.

Figure 1:
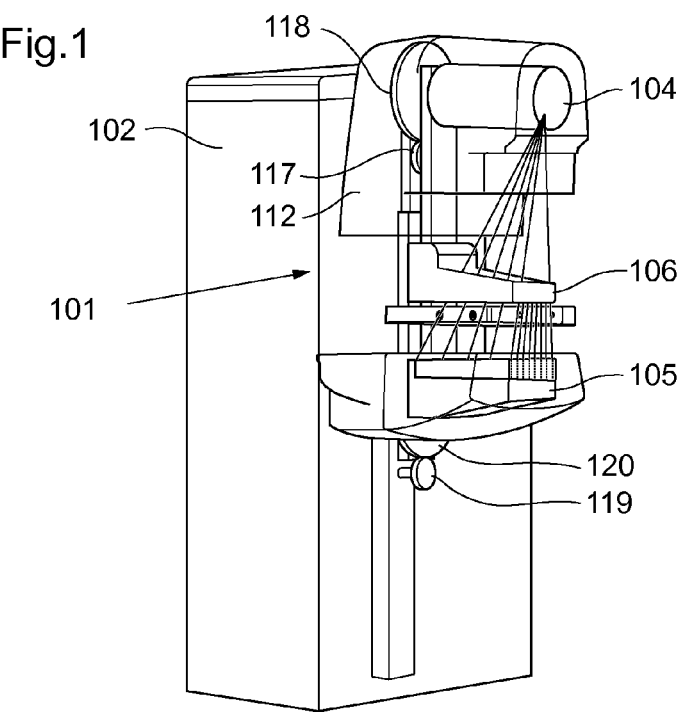
FIG. 1 illustrates a schematic view of an x-ray imaging system

FIG. 1 illustrates an x-ray imaging system (101, 201, 301) schematically according to one embodiment, wherein the system comprising an x-ray apparatus (102, 202, 302). The x-ray apparatus (102, 202, 302) further comprising a scan arm (103, 203, 303), wherein an x-ray source (104, 204, 304) is arranged on one upper portion (112, 212, 312) of the scan arm (103, 203, 303) but may be arranged at any position along the scan arm (103, 203, 303) according to other embodiments of the invention. A detector (105, 205, 305) is arranged in the other, lower end of the scan arm (103, 203, 303), the detector (105, 205, 305) comprising a plurality of detectors strips (105a, 205a, 305a). The detector (105, 205, 305) may however be arranged at any position along a scan arm (103, 203, 303) according to other embodiments of the invention. A collimator (106, 206, 306) comprising a plurality of slits (106a, 206a, 306a) is arranged between the x-ray source (104, 204, 304) and the detector (105, 205, 305) on the scan arm (103, 203, 303). In an arrangement, separate from the scan arm (103, 203, 303) and any motion thereof, the x-ray apparatus (102, 202, 302) further comprises at least one position adjustable compression paddle (107a, 107b; 207a, 207b; 307a, 307b) for compressing and fixating an object (108, 208, 308), such as a breast, during a scan.

Figure 2:
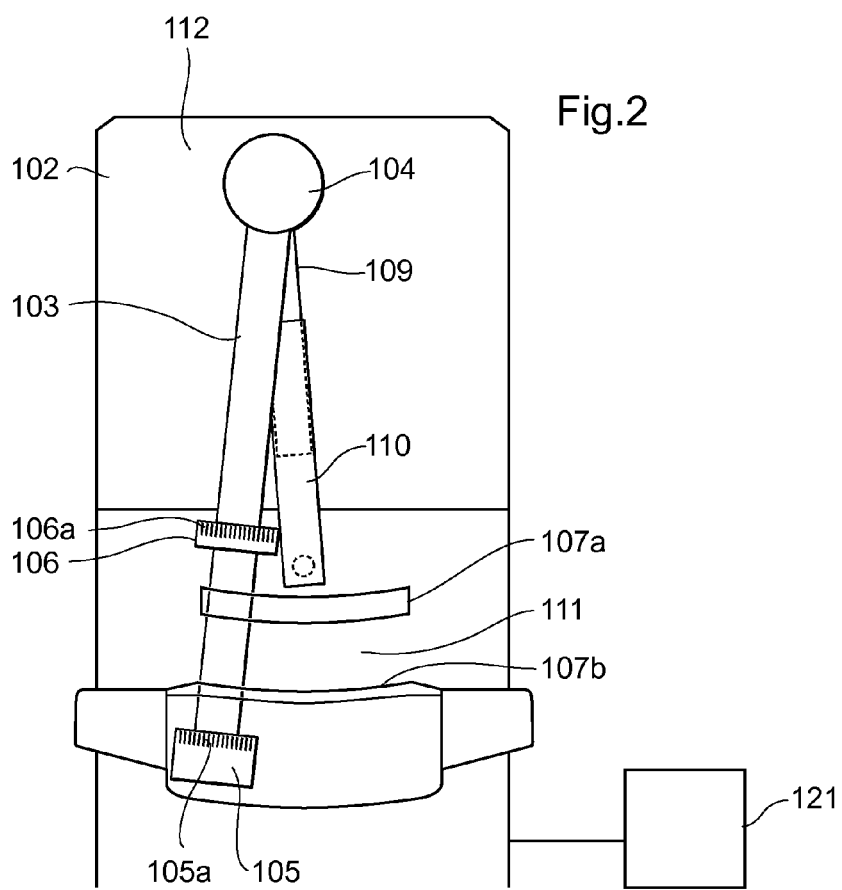
FIG. 2 shows a schematic view of the x-ray apparatus wherein the arrangement and parts of the apparatus are explained

FIG. 2 shows a schematic view of the x-ray apparatus (102, 103), according to one embodiment, wherein the arrangement and parts of the apparatus that enables both 2D scan motions and 3D scan motions are further explained. As seen in the figure, the x-ray source (104, 204, 304) is pivotally arranged in a first end of a first suspension arm (109, 209, 309). The first end (109a, 209a, 309a) of the first suspension arm (109, 209, 309) may be pivotally arranged in a an upper portion (112, 212, 312) of the x-ray apparatus. The second end (109b, 209b, 309b) of the first suspension arm (109, 209, 309) is arranged linearly displaceable in relation to a first end (110a, 210a, 310a) of a second suspension arm (110, 210, 310), in a manner such that the total length of the first (109, 209, 309) and second suspension arm (110, 210, 310) may be varied. According to one embodiment, the first suspension arm (109, 209, 309) is arranged partly inside the second suspension arm (110, 210, 310), however the arrangement may be the other way around, i.e. wherein the second suspension arm (110, 210, 310) is partly arranged inside the first suspension arm (109, 209, 309). Further, the second end (110b, 210b, 310b) of the second suspension arm (110, 210, 310) is pivotally arranged in a lower portion (111, 211, 311).

In order to control a movement of the x-ray source (104, 204, 304) in a horizontal direction, a first linear screw (not shown) may be is arranged in x-ray apparatus (102, 202, 302) and connected in one end to the upper portion (112, 212, 312) near the x-ray source (104, 204, 304). A corresponding second linear screw (not shown) may be arranged in the lower portion (112, 212, 312) and connected to the detector (105, 205, 305) to control the movement of the detector (105, 205, 305) in a horizontal direction. A third linear screw (not shown) may be arranged in first and/or second suspension arm (110, 210, 310) in order to control the total length of the first and second suspension arm (110, 210, 310). Any suitable type of actuation mechanism may however be used that enables the horizontal movements between the parts described. The actuation mechanism may for instance comprise motors driving of various size arranged at various positions on the x-ray apparatus. Such actuation mechanisms is seen schematically in FIG. 1, and is also further explained in connection to FIG. 20, FIG. 21 and FIG. 22.

In order to control the rotational movement of the scan arm (103, 203, 303) in relation to the first suspension arm (109, 209, 309), a first motor (116, 216, 316), preferably of electrical kind, is arranged, preferably on the first suspension arm (109, 209, 309), wherein a first sprocket (117, 217, 317) is adapted to be rotated upon the activation of the first motor (116, 216, 316) in one of two rotational directions. A second sprocket (118, 218, 318), preferably larger than the first sprocket (117, 217, 317), is arranged on the scan arm (103, 203, 303) in order to be engaged with the first sprocket (117, 217, 317), wherein a rotational movement of the first sprocket (117, 217, 317) is transferred to the second sprocket (118, 218, 318) and to the scan arm (103, 203, 303). A second motor (126, 226, 326), preferably an electrical motor and similar to the first motor (116, 216, 316), is arranged in the lower portion (111, 211, 311) or in another part of the x-ray apparatus (102, 103), wherein a third sprocket (120, 220, 320) is arranged to be rotated upon the activation of the motor in one of two rotational directions. A fourth sprocket (120, 220, 320), preferably larger than the third sprocket (119, 219, 319) is arranged on the second suspension arm (110, 210, 310) in order to be engaged with the third sprocket (119, 219, 319), wherein a rotational movement of the third sprocket (119, 219, 319) is transferred to the fourth sprocket (120, 220, 320) and to the second suspension arm (110, 210, 310). A control unit (121, 221, 321) is connected to the motors (116, 216, 316, 119, 219, 319) in order to control the motors and thereby the rotational movement of the first/second suspension arm (110, 210, 310), and the scan arm (103, 203, 303). By the aid of this arrangement, the arbitrary movement in two dimensions of the x-ray source (104, 204, 304) and the detector (105, 205, 305) is enabled within the mechanical restraints of the rotational limits between the scan arm (103, 203, 303) and the first suspension arm (109, 209, 309), the varying of the total length of the first and second suspension arm (110, 210, 310), and the connection between the x-ray source (104, 204, 304) and the detector (105, 205, 305) through the scan arm (103, 203, 303). In the embodiment wherein a scan arm (103, 203, 303) is not present, an additional degree of freedom in the relative movement between the x-ray source (104, 204, 304) and the detector (105, 205, 305) is present. When the detector (105, 205, 305) and x-ray source (104, 204, 304) are connected by a scan arm (103, 203, 303), an x-ray beam (122, 222, 322) irradiated or emitted from the x-ray source (104, 204, 304) is thus set to be directed towards, i.e. aligned with and irradiate or emit, the detector (105, 205, 305). In any embodiment wherein no scan arm (103, 203, 303) is present, and the absolute distance between the x-ray source (104, 204, 304) and the detector (105, 205, 305) may vary, a control unit (121, 221, 321) is adapted to rotate the x-ray source (104, 204, 304) and the detector (105, 205, 305) such that x-ray beams emitted from the x-ray source (104, 204, 304) is adapted to be directed towards, and irradiate the detector (105, 205, 305). The words "irradiate" and "emit" is used interchangeably throughout the application.

During the scan movement of the x-ray source (104, 204, 304) and the detector (105, 205, 305) in relation to an object, the x-ray source (104, 204, 304) may thus be moved along an arbitrary first movement path that may be redefined at any instant in time and between different scans as well as being rotated during this movement. In a similar manner, the detector (105, 205, 305) may be moved along an arbitrary second movement path that may be redefined at any instant in time and between different scans, as well as being rotated during this movement. Further, throughout this application, a scan movement will be referred to as the movement of the x-ray source (104, 204, 304) and/or the detector (105, 205, 305) assembly along a first and a second movement path. The scan movement further comprises a subset when the irradiated x-rays are actually impinging on an object (108, 208, 308) wherein an image of the objected can be reconstructed. Such movements are hereinafter referred to as a scan of an object, or alternatively, object scan. A scan movement may comprise movements of the x-ray source and detector necessary for reconstruction of an image volume, i.e. tomosynthetic images or at least a slice of an image volume of the object. Such scan movement requires a scan movement comprising various projection angles through the same point in an object, so called tomo-angles, or tomographic angles or tomographic projection angles, and their spread is often referred to as tomographic angle, which is related to vertical resolution. These angles may vary across the image field, whereby the acquired 3d image may have local variations in characteristics. According to one embodiment, scan movement further comprises that the x-ray source emits an x-ray beam towards the detector with the purpose of generating x-ray images.

Figure 3:
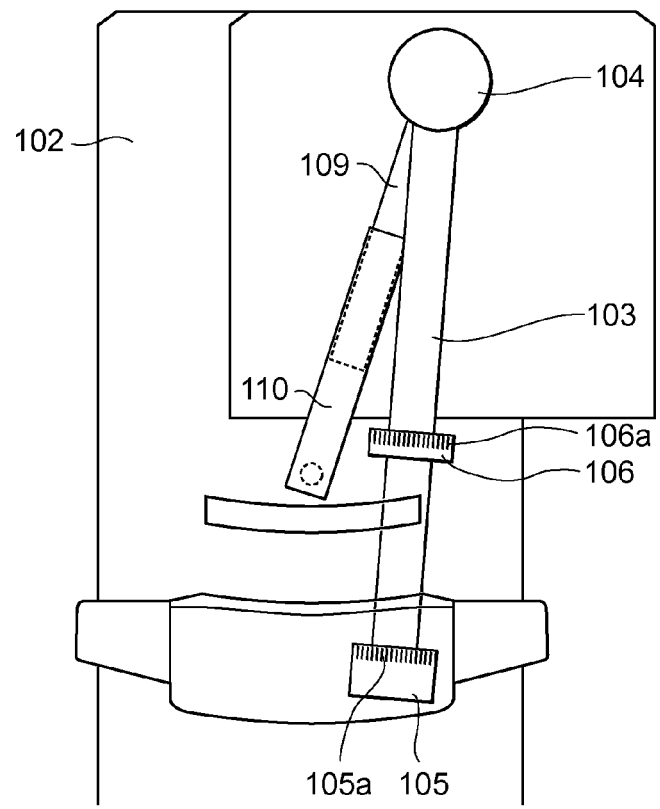
FIG. 3 shows an example of a possible position of the scan arm

In FIG. 3, an example of a possible position of the scan arm (103, 203, 303), and thus the relation of the x-ray source (104, 204, 304) in relation to the detector (105, 205, 305) is shown, by the aid of the arrangement described above, controlling the movement of the x-ray source (104, 204, 304) and the detector (105, 205, 305). The first and second linear screws (not shown), have moved the detector (105, 205, 305) as well as the x-ray source (104, 204, 304) portion to the right in FIG. 3. Further, the actuation of the third linear screw (115, 215, 315) has increased the total length of the first and second suspension arm (110, 210, 310), wherein the x-ray source (104, 204, 304) has moved to a position upwards and to the right in the figure. Naturally, the same movement may be achieved by the actuation of sprockets 1-4 in combination with the linear screw of the first and second suspension arm (110, 210, 310).

Figure 4A:
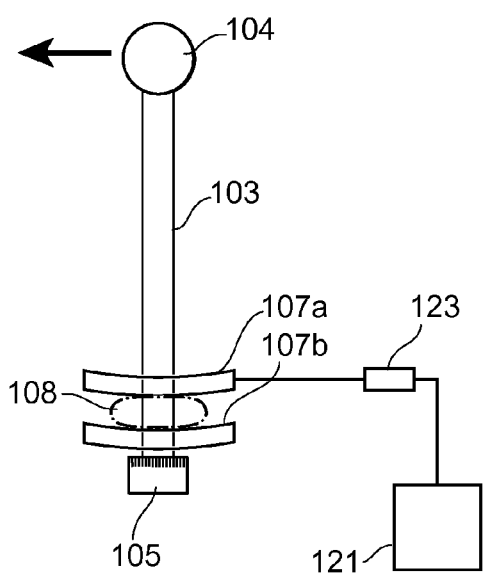
FIG. 4a shows an embodiment of the invention comprising a position adjustable compression paddle

FIG. 4a shows an embodiment of the invention comprising a position adjustable compression paddle (107a, 107b; 207a, 207b; 307a, 307b) and a means for measuring the position (123, 223, 323), preferably the height position, of the compression paddle (107a, 107b; 207a, 207b; 307a, 307b) in relation to a fixed point in space. The means for measuring the position (123, 223, 323) of the compression paddle (107a, 107b; 207a, 207b; 307a, 307b) is connected to the control unit (121, 221, 321) for controlling the movement of the x-ray source (104, 204, 304) and the detector (105, 205, 305), for instance via a cable (124, 224, 324) or via wireless transmission. The means for measuring the position (123, 223, 323) of the compression paddle (107a, 107b; 207a, 207b; 307a, 307b) is adapted to output data corresponding to the position of the compression paddle (107a, 107b; 207a, 207b; 307a, 307b) to the control unit (121, 221, 321). The control unit (121, 221, 321) is adapted to receive such data, also referred to as external data throughout this application, wherein the control unit (121, 221, 321) is adapted to control the movement of the x-ray source (104, 204, 304) and the detector (105, 205, 305) based on this external data.

Figure 4B:
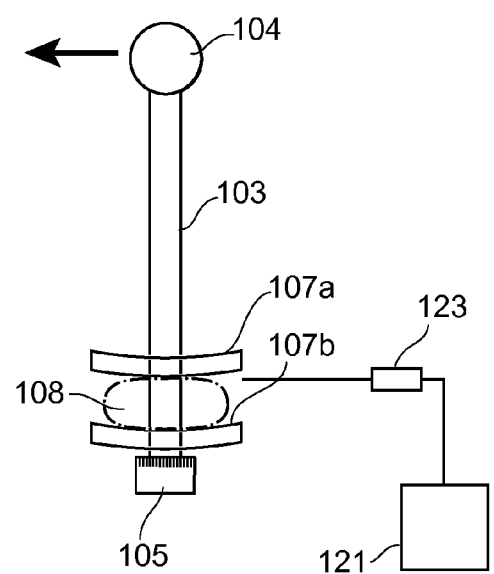
FIG. 4b shows the compression paddle having a position higher than that of FIG. 4a FIG. 5a-5b shows an embodiment, wherein the position of the compression paddle comprises external data

One example of how the control unit (121, 221, 321) controls the movement of the x-ray source (104, 204, 304) can be seen in the example of FIG. 4a and FIG. 4b. According to the embodiment of FIG. 4a, a scan of an object (108, 208, 308) is initiated wherein at least the x-ray source (104, 204, 304) travels with a speed v defined by the control unit (121, 221, 321) based on the position of the compression paddle (107a, 107b; 207a, 207b; 307a, 307b). In FIG. 4b, the compression paddle (107a, 107b; 207a, 207b; 307a, 307b) has a position higher than that of 4b wherein the control unit (121, 221, 321) sets a lower speed of at least the x-ray source (104, 204, 304) during the scan. Hence, the control unit (121, 221, 321) is adapted to set a lower speed of the x-ray source (104, 204, 304) if the compression paddle (107a, 107b; 207a, 207b; 307a, 307b) is relatively high compared to another lower position of the compression paddle.

According to one embodiment, if the x-ray source (104, 204, 304) and the detector (105, 205, 305) moves with respective speeds along their first and second movement paths, the control unit (121, 221, 321) is adapted to control the speed of the x-ray source (104, 204, 304) such that the ratio between the speed of the x-ray source (104, 204, 304) and the detector (105, 205, 305) is high enough to allow the x-ray source (104, 204, 304) to pass the detector (105, 205, 305) in horizontal direction at least during the scan of an object.

Figure 5A:
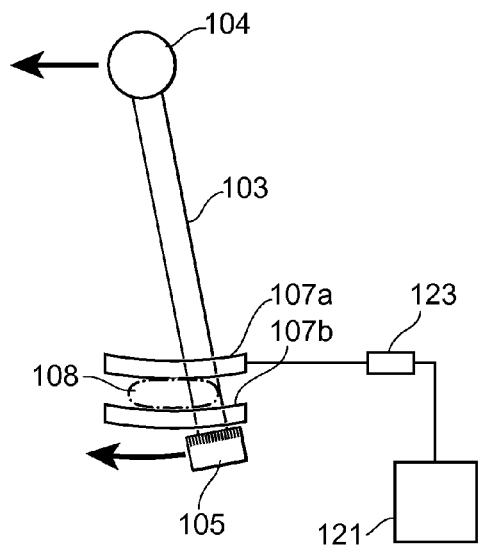
Figure 5B:
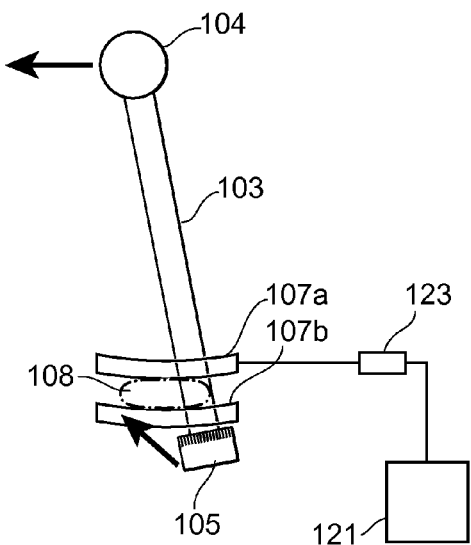

In FIG. 5a and FIG. 5b a further aspect of the invention is shown. The control unit (121, 221, 321) is adapted to control the movement of the x-ray source (104, 204, 304) and the detector (105, 205, 305) based on input from external data comprising the position of at least one compression paddle (107a, 107b; 207a, 207b; 307a, 307b) such that a collision between the detector (105, 205, 305) and the compression paddle (107a, 107b; 207a, 207b; 307a, 307b) is prevented. Hence, a collision is avoided when the second movement path is not crossing the position of the compression paddle (107a, 107b; 207a, 207b; 307a, 307b), i.e. when the compression paddle (107a, 107b; 207a, 207b; 307a, 307b) is outside the second movement path. In FIG. 5a a portion of the first and second movement paths are shown, wherein the lower compression paddle (107a, 107b; 207a, 207b; 307a, 307b) is outside the second movement path and a collision is avoided. FIG. 5b, to the contrary, shows an un-allowed control of the movements of the x-ray source (104, 204, 304) and the detector (105, 205, 305) wherein the compression paddle (107a, 107b; 207a, 207b; 307a, 307b) is in the way of the second movement path and a collision will eventually occur.

Figure 6A:
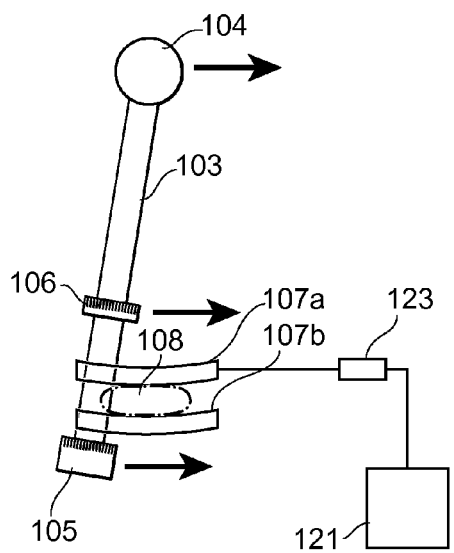
FIG. 6a-6b shows an embodiment, similar to that of FIG. 5a-5b wherein a collimator is arranged on the scan arm
Figure 6B:
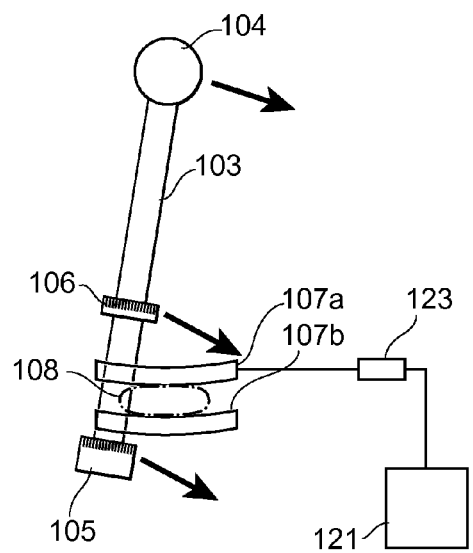

FIG. 6a and FIG. 6b show an analogous set up as in FIGS. 5a and 5b with the slight difference of the addition of a collimator (106, 206, 206). The control unit (121, 221, 321) is adapted to control the movement of the x-ray source (104, 204, 304) and the detector (105, 205, 305) based on the input from external data comprising the position of at least one compression paddle (107a, 107b; 207a, 207b; 307a, 307b) such that a collision between the collimator (106, 206, 306) and the compression paddle (107a, 107b; 207a, 207b; 307a, 307b) is avoided. In analogy to the defined movement paths of the x-ray source (104, 204, 304) and the detector (105, 205, 305), the collimator (106, 206, 306) will move along a third movement path being defined by the first and second movement paths. Hence, collision is avoided when the third movement path is not crossing the position of the compression paddle (107a, 107b; 207a, 207b; 307a, 307b), i.e. when the compression paddle (107a, 107b; 207a, 207b; 307a, 307b) is outside the third movement path. In FIG. 6a a portion of the first, second and third movement paths are shown, wherein the compression paddle (107a, 107b; 207a, 207b; 307a, 307b) is outside the third movement path and a collision is avoided. FIG. 6b, to the contrary, shows an un-allowed control of the movements of the x-ray source (104, 204, 304) and the detector (105, 205, 305) wherein the upper compression paddle (107b, 207, 307b) is in the way of the third movement path and a collision will eventually occur.

Figure 7A:
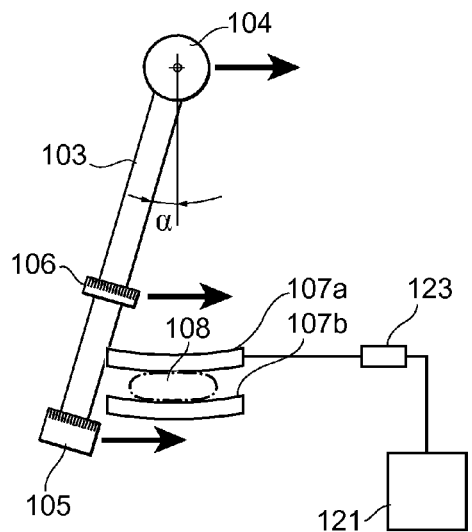
FIG. 7a-7b shows scan movements wherein an angle α is defined
Figure 7B:
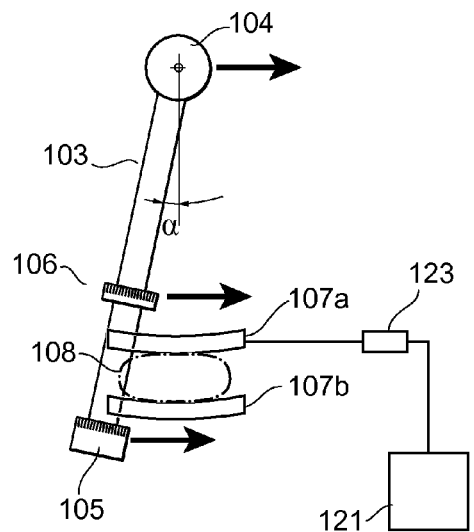

In FIG. 7a, another type of scan movement possible with the x-ray apparatus (102, 202, 302) according to this invention is shown. Herein, an angle α of the scan arm (103, 203, 303) in relation to a vertical line, is essentially unchanged during the entire scan movement. The angle α is set during the start of the scan movement by the control unit (121, 221, 321) taking the height position of the compression paddle (107a, 107b; 207a, 207b; 307a, 307b) into consideration, wherein the angle α of the is roughly inversely proportional to said height position, depending on shape of the paddle and patient support. As can be seen in FIG. 7b, the angle α of the scan arm (103, 203, 303) is set smaller for a scan movement by the control unit (121, 221, 321) when the latter senses a high position of the compression paddle (107a, 107b; 207a, 207b; 307a, 307b). Hereby, an unwanted collision between the collimator (106, 206, 306) and the compression paddle (107a, 107b; 207a, 207b; 307a, 307b) is avoided. In another embodiment, the control unit (121, 221, 321) is adapted to control the movement of the x-ray source (104, 204, 304) and the detector (105, 205, 305) such that the angle α of the scan arm (103, 203, 303) does not exceed a limit value, wherein the limit value is constantly varying with the positions of the x-ray source (104, 204, 304) along a first movement path and the detector (105, 205, 305) along a second movement path and based on the height position of the compression paddle (107a, 107b; 207a, 207b; 307a, 307b). For instance, in addition to the general control of the scan arm (103, 203, 303) to allow a smaller angle α due to a high position of the compression paddle (107a, 107b; 207a, 207b; 307a, 307b), a relatively higher position of the scan arm (103, 203, 303) would allow a somewhat larger angle than a relatively lower position of the scan arm (103, 203, 303), wherein the collision between the collimator (106, 206, 306) and the compression paddle (107a, 107b; 207a, 207b; 307a, 307b) would still be prevented.

According to another embodiment of the invention, the detector (105, 205, 305) is adapted to sense characteristics of a received x-ray beam (122, 222, 322) from the x-ray source (104, 204, 304) in real time during the entire scan movement. The detector (105, 205, 305) is further adapted to output said data wherein the control unit (121, 221, 321) controlling the movement of the x-ray source (104, 204, 304) and the detector (105, 205, 305) is connected to the detector (105, 205, 305) by for instance a cable (124, 224, 324) or wireless transmission wherein said data, also referred to as external data, can be received by the control unit (121, 221, 321), wherein the control unit (121, 221, 321) uses said external data for controlling a remainder of the scan movement.

Figure 8A:
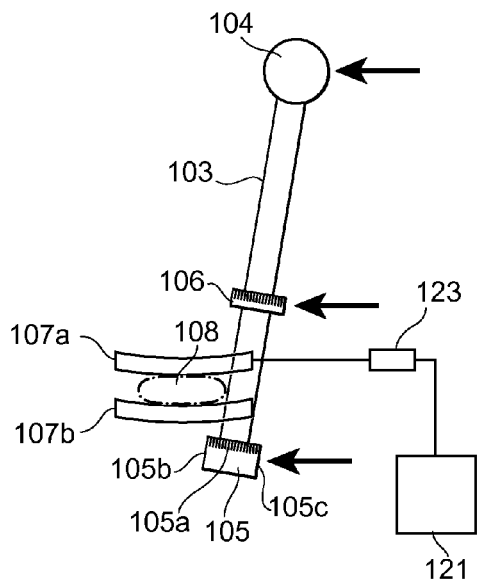
FIG. 8a-8b, shows an embodiment wherein external data comprises data from the detector FIG. 9 describes a scan movement around an identified interesting area in an object
Figure 8B:
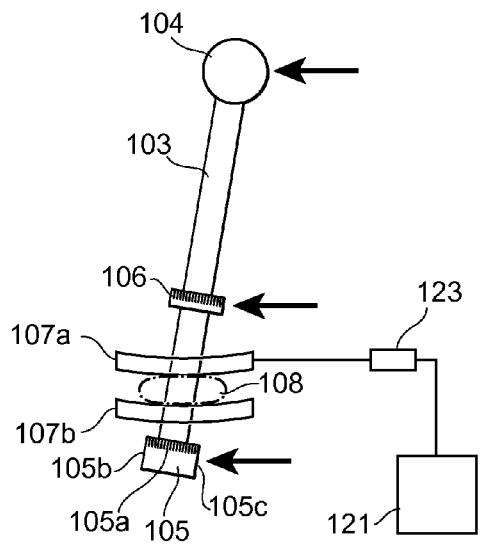
Figure 11A:
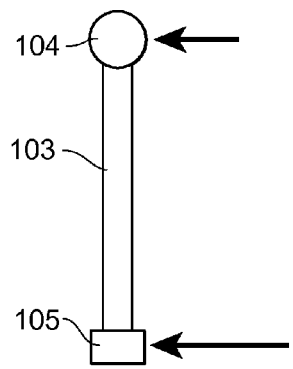
Figure 11B:
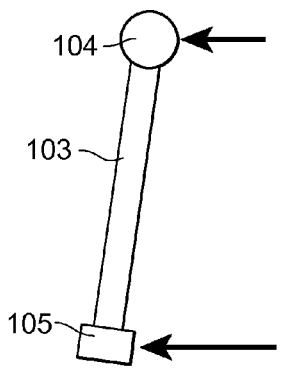
Figure 11C:
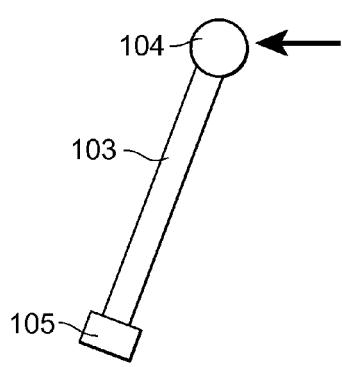
Figure 11D:
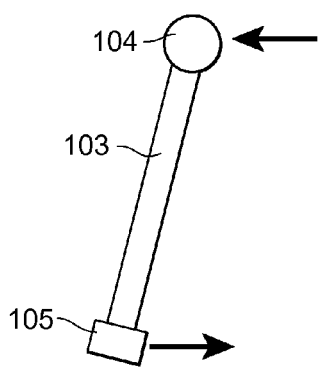

As seen in FIG. 8a, the detector (105, 205, 305) has a first (105b, 205b, 305b) and second end (105c, 205c, 305c) wherein a plurality of detector lines (105a) are arranged between said first and second ends. The detector (105, 205, 305) is adapted to receive impinging photons from the x-ray source (104, 204, 304) during a scan movement, and the detector (105, 205, 305) is further being adapted to count each photon impinging on the detector (105, 205, 305) above a certain energy threshold by generating a signal corresponding to the energy of each impinging photon. During a scan of an object, fewer impinging photons per time frame above said threshold will reach the detector (105, 205, 305) compared to the rest of the scan movement when no object (108, 208, 308) placed in the x-ray beam in order to be scanned, attenuates photons from the x-ray beam. In other words, the x-ray intensity, or count rate, of the photons is lower once a scan of an object (108, 208, 308) starts compared to the rest of a scan movement. Other methods of establishing or detecting the x-ray intensity is also known in the art, such as for instance measuring the total charge readout at during a time frame etc. According to this embodiment, such information is used by the control unit (121, 221, 321) for controlling the movement of the x-ray source (104, 204, 304) and the detector (105, 205, 305). In the same figure a scan movement of an x-ray source (104, 204, 304) and a detector (105, 205, 305) is illustrated along with an object (108, 208, 308) compressed between two compression paddles (107a, 107b; 207a, 207b; 307a, 307b) is seen wherein the scan arm (103, 203, 303) moves to the left with a certain speed. The scan movement shown has just recently become a scan of an object. This phase of the scan movement is sensed by the detector lines (105a, 205a, 305a) being arranged closer to the first end of the detector (105, 205, 305), arranged essentially in the left part of the detector (105, 205, 305) as they sense a lower count rate due to the attenuation of photons in the object. This information, or data, is sent to the control unit (121, 221, 321) for controlling the remainder of the scan motion. As seen in FIG. 8b, according to one embodiment, the speed of at least the x-ray source (104, 204, 304) thereby decreases during the remainder of the scan of the object (108, 208, 308) to a preset speed which is related to the actual count rate sensed by the detector (105, 205, 305). Essentially, the speed of the x-ray source will be lowered even more than the x-ray source during a scan of an object, such that a higher ratio between the speed of the x-ray source and the detector is achieved. Hereby, the tomographic angles for each point in the object is increased, which is relevant when reconstructing tomosynthesis images over the relevant object. At the same time, by allowing a having a higher speed of the x-ray source and the detector during a scan movement which is not an object scan, time for performing the entire scan movement will be decreased. This is beneficial not the least when considering the large amount of investigations that need to be performed during a mammographic screenings. Data concerning the relationship between sensed count rate and speed may be saved in a table format into a memory device of in or in connection to the control unit (121, 221, 321) and used by the control unit (121, 221, 321) upon controlling the movement. In any part of the scan movement that is not a scan of the object, the speed of the at least the x-ray source (104, 204, 304) may be increased again before the scan of the object (108, 208, 308) in order to lower the time required to perform the scan. Further, the control unit (121, 221, 321) is adapted to control the movement of the x-ray source (104, 204, 304) and the detector (105, 205, 305) such that the ratio between their respective speeds are high enough to allow the x-ray source (104, 204, 304) to pass the detector (105, 205, 305) in a horizontal direction during the scan of an object (108, 208, 308) as sensed by the detector (105, 205, 305).

According to another embodiment of the invention, as seen in FIG. 9, the control unit (121, 221, 321) is further adapted to control the movement of the x-ray source (104, 204, 304) and the detector (105, 205, 305) based on the detector (105, 205, 305) identifying an interesting area of the object, e.g. a suspected abnormality in a breast, wherein a certain predefined scan movement is performed or wherein the speed of at least the x-ray source (104, 204, 304) decreases to enhance ability to further analyze this area. The interesting area is seen as a dark spot in the object (108, 208, 308) This identification may be performed during the actual scan of the object, but may also have been performed during a previous scan directly before-hand, or alternatively at a different screening at a time when an interesting area in an object was identified. The positions of the x-ray source and the detector for performing a scan movement over this area alone requires saving of data corresponding to these predefined positions. In the latter cases, the external data used by the control unit (121, 221, 321) may be saved into a database wherein this database is accessible by the control unit (121, 221, 321). These type of scans performed over an interesting spot is normally referred to as a spot scan. According to one embodiment, the x-ray source and the detector decreases their both their speeds when reaching the interesting area, in such way that the ratio between the speed of the x-ray source and the detector increases such that larger tomographic angles are achieved.

What is said above for the capacity of the detector (105, 205, 305) to sense when an object (108, 208, 308) is scanned can be implemented and used together with any of the embodiments described in connection to the controlling of the movement based on the presence of a compression paddle.

In the following, different scan movements will be described, that may serve to optimize the tomo-angles based on external data according to certain embodiments:

FIG. 10a-FIG. 10e illustrates a schematic view of the scan arm (103, 203, 303) comprising an x-ray source (104, 204, 304) and the detector (105, 205, 305) and one preferred scan movement. The directions and sizes of the arrows represent the directions and speed of the x-ray source (104, 204, 304) and the detector (105, 205, 305). A lack of arrows represents a zero speed of the x-ray source or the detector. Turning points of the x-ray source and the detector comprises a position wherein the x-ray source or detector changes direction from a first to a second direction wherein the second direction is essentially opposite the first direction. In FIG. 10a, both the x-ray source (104, 204, 304) and the detector (105, 205, 305) travel to towards their first turning points, wherein the x-ray source (104, 204, 304) has a speed than the detector (105, 205, 305), i.e. wherein the ratio between the speed of the x-ray source (104, 204, 304) and the detector (105, 205, 305) is around 2. In FIG. 10b, the x-ray source (104, 204, 304) has passed the detector (105, 205, 305) in a horizontal direction due to the higher speed. In FIG. 10c, the x-ray source (104, 204, 304) has reached the first turning point along the first movement path, whereas the detector (105, 205, 305) continues a movement towards the first turning point along the second movement path. In FIG. 10d the x-ray source (104, 204, 304) turns direction essentially into an opposite direction as prior to reaching the turning point, wherein the speed of the x-ray source (104, 204, 304) is increased to a similar speed had prior to reaching the turning point, essentially instantaneously after turning. This requires a relatively high acceleration of x-ray source (104, 204, 304), according to one embodiment, the acceleration is in the range of 1 m/s$^2$. In the same scan, the x-ray source (104, 204, 304) and the detector (105, 205, 305) may travel towards the second turning points along the first and second movement paths and perform a corresponding motion as described above.

FIG. 10e represents the scan movement of FIG. 10a-10d wherein the achieved tomo-angle is shown. The movement of the x-ray source along a first movement path and the movement of the detector along the second movement path, corresponds to a combined movement path, wherein said combined movement path can be represented by a curve through a multi-dimensional parametric space involving a position along one axis and an angle between said x-ray source and detector as seen in the figure. The three dots represent the position of a bundle of three x-rays, corresponding to three detector lines (105a) of the detector (105, 205, 305), thus impinging into the detector (105, 205, 305) with three different angles, wherein the middle ray impinges the detector (105, 205, 305) with an angle=0. The position along the object (108, 208, 308) being scanned is represented by the x-axis. The varying ray angle of the x-ray source (104, 204, 304) and the detector (105, 205, 305) relative a vertical line corresponding to the middle ray of the three shown rays impinging on the detector (105, 205, 305) is shown along the y-axis $v_r$, and thus implicitly represents a position of the x-ray source (104, 204, 304) in relation to the detector (105, 205, 305). The tomo-angle achieved during a scan movement between two position of the x-ray detector (105, 205, 305) is represented by the distance $v_t$, i.e. the spread of local tomographic projection angles.

The lowermost position to the left of the three dots, i.e. in the third quadrant, corresponds to FIG. 10a, wherein the detector (105, 205, 305) is slightly to the left of the x-ray source (104, 204, 304) scanning a left portion of the object. The position of the three detector lines in the second quadrant represents a position of the scan arm (103, 203, 303) corresponding to that shown in FIG. 10c, i.e. when the x-ray source reaches the turning point. FIG. 10b would correspond to a position between that just described and the x-axis. FIG. 10d corresponds to a position wherein $v_r$ is zero and the middle of the object (108, 208, 308) is scanned. The continued scan movement towards the right portions of the object, are represented by the dots in the first and fourth quadrants. This part of the scan movement is not further explained here as it is a mirroring of the movement in the just described. From FIG. 10e, the importance of the ratio between the speeds of the x-ray source (104, 204, 304) and the detector (105, 205, 305) is seen for the tomo-angle. The larger the ratio, and hence the steepness of the lines between two positions of the detector (105, 205, 305), the larger the tomo-angle can be achieved. Hence, the scan movement right after the x-ray source turns, wherein the x-ray source (104, 204, 304) is sharply accelerated, is essential for achieving large and optimized tomo-angles.

FIG. 11a-FIG. 11d represents a similar scan movement to that described in FIG. 10a-10d, with the difference that the detector (105, 205, 305) reaches the first turning point before the x-ray source (104, 204, 304). The scan movement is therefore not further explained here.

Figure 12A:
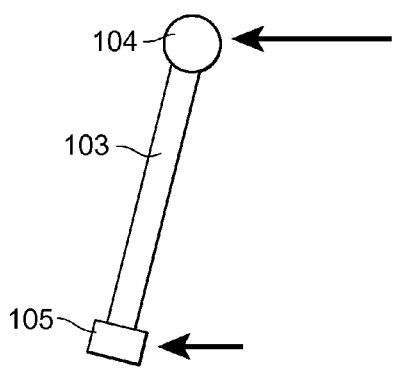
FIG. 12a-12f illustrates a schematic view of the scan arm at certain positions of the scan arm during scan movement at a turning point
Figure 12B:
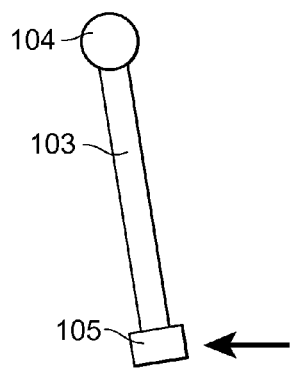
Figure 12C:
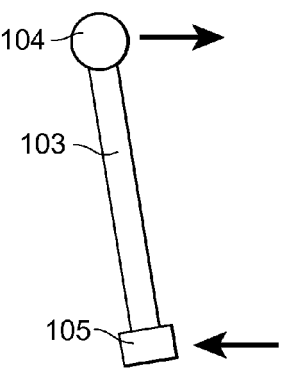
Figure 12D:
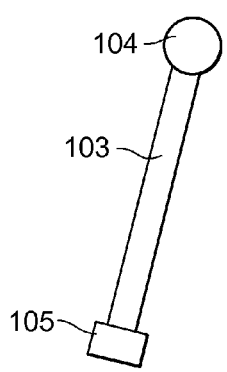
Figure 12E:
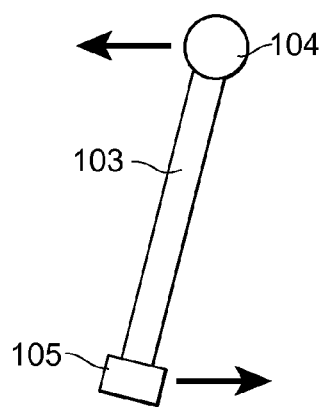
Figure 12F:
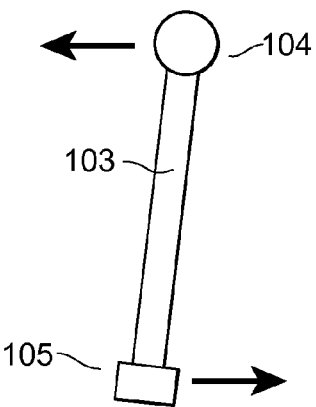

FIG. 12a-12g illustrates a schematic view of the scan arm (103, 203, 303) comprising an x-ray source (104, 204, 304) and the detector (105, 205, 305) and another preferred scan movement. The directions and sizes of the arrows represent the directions and speed of the x-ray source (104, 204, 304) and the detector (105, 205, 305). In FIG. 12a, both the x-ray source (104, 204, 304) and the detector (105, 205, 305) travel to towards their first turning points, wherein the x-ray source (104, 204, 304) has a higher speed than the detector (105, 205, 305). In FIG. 12b, the x-ray source (104, 204, 304) has passed the detector (105, 205, 305) in a horizontal direction due to the higher speed and reached a turning point of the first movement path, wherein the detector (105, 205, 305) continues the movement towards its first turning point along a second movement path. In FIG. 12c the x-ray source (104, 204, 304) turns direction essentially in an opposite direction as prior to reaching the turning point, wherein the speed of the x-ray source (104, 204, 304) is increased to a similar speed had prior to reaching the turning point, essentially instantaneously after the turning. This requires a high acceleration of x-ray source (104, 204, 304), in the range of 1 m/s$^2$. In the same figure, the detector (105, 205, 305) continues the movement towards its first turning point along a second movement path. In FIG. 12d the x-ray detector (105, 205, 305) has reached its first turning point along the second movement path, and essentially simultaneously, the movement of the x-ray source (104, 204, 304) along the first movement path is stopped. In FIG. 12e, the x-ray source (104, 204, 304) again accelerates steeply towards the first turning point, wherein simultaneously, the detector (105, 205, 305) moves towards the second turning point along the second movement path, accelerating steeply. In FIG. 12f, the x-ray source (104, 204, 304) and the detector (105, 205, 305) has moved along their essentially opposite directions, such that the x-ray is now closer to the first turning point than the detector (105, 205, 305). i.e. the angle $v_r$ is again positive.

In the same scan, the x-ray source (104, 204, 304) and the detector (105, 205, 305) may travel towards the second turning points along the first and second movement paths and perform a corresponding motion as described above.

Figure 12G:
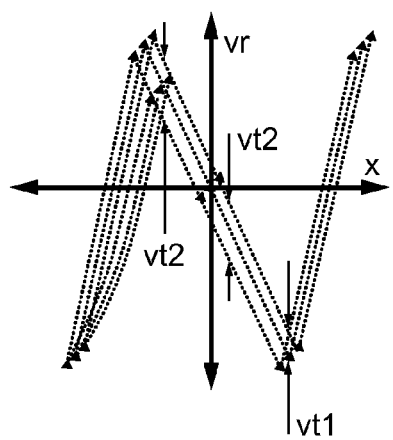
FIG. 12g shows the achieved tomo-angles during the scan movement according to FIG. 12a-12f

FIG. 12g represents the scan movement of FIG. 12a-12e wherein the achieved tomo-angle is shown with references similar to those described in FIG. 10e. The lowermost position to the left of the three dots, i.e. in the third quadrant, corresponds to FIG. 12a, wherein the detector (105, 205, 305) is slightly to the left of the detector (105, 205, 305) scanning a left portion of the object. The position of the three detector lines in the second quadrant represents a position of the scan arm (103, 203, 303) corresponding to that shown in FIG. 12b, i.e. when the x-ray source reaches the turning point. FIG. 12d, wherein the detector (105, 205, 305) has reached its turning point along the second movement path corresponds to essentially the same position as when the scan started, i.e. the dots are overlapping the dots in the third quadrant. The movement in opposite direction by the x-ray source (104, 204, 304) and the detector (105, 205, 305) such that the x-ray is now closer to the first turning point than the detector (105, 205, 305) corresponding to FIG. 12*f* is represented by the second set of three dots in the second quadrant positioned slightly to the right and with a little smaller angle $v_r$. Through this scan movement, a uniform tomo-angle around the turning point can be achieved, wherein $v_{t2}=v_{t0}$. Compared for instance with $v_{t1}$ which is similar to the tomo-angles as achieved in the turning points in FIG. 12*g*, and smaller than $v_{t0}$. Without the scan movement according to FIG. 12*q*, the image quality will be poorer for this part of the object. A big tomo-angle is achieved in a left part of the scan corresponding to the position of FIG. 12*f*, i.e. left of the $v_{t2}$ position. As can further be seen in the same figure, the right part of the scan is different compared to the left part of the scan, wherein the detector (105, 205, 305) is not changing direction in its second turning point. It thus corresponds to the right part of the scan as seen in FIG. 12*e*. It can further be noted that some of the angles are scanned twice in the left part of the scan seen by the overlapping of rays. The scanning of such superfluous angles can be masked by a suitable field limiter covering the relevant detector lines (105*a*, 205*a*, 305*a*).

Figure 13:
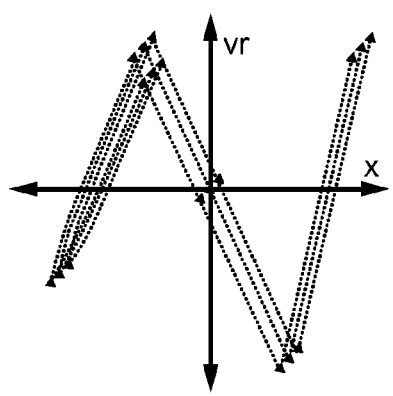
FIG. 13 shows an alternative scan movement, wherein the tomo-angle is slightly smaller compared to in FIG. 12g FIG. 14a-FIG. 14f represents a similar scan movement to that described in FIG. 12a-12f
Figure 14A:
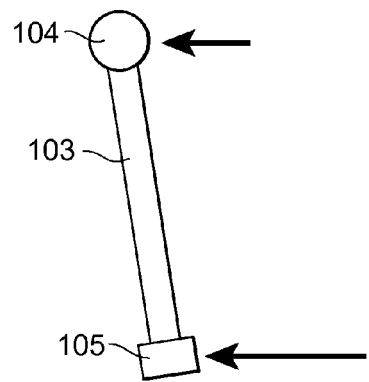
Figure 14B:
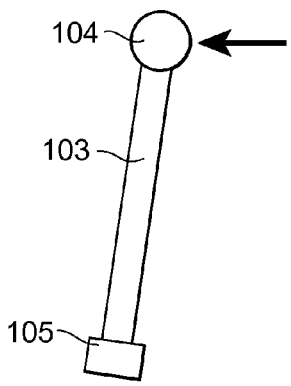
Figure 14C:
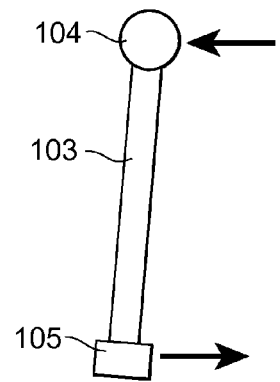
Figure 14D:
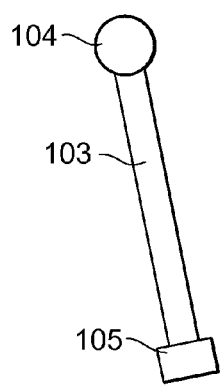
Figure 14E:
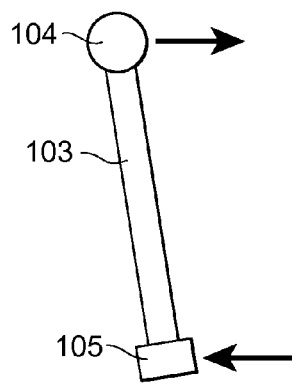
Figure 14F:
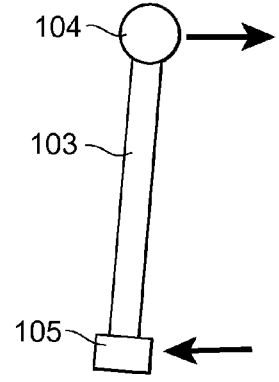

FIG. 13 shows an alternative scan movement, wherein the tomo-angle is slightly smaller compared to in FIG. 12*g*. This is achieved by reducing the relative speed between the x-ray source (104, 204, 304) and the detector (105, 205, 305), i.e. the ratio between the speed of the x-ray source and the detector. Such scan movement may be preferred and optimal for a relatively thicker breast, wherein aliasing problems may occur if the tomo-angles are to large. Thus, the control unit may use the external data such as the position of the compression paddle, or data concerning x-ray intensity, to move the x-ray source and detector according to this scan movement.

FIG. 14*a*-FIG. 14*f* represents a similar scan movement to that described in FIG. 12*a*-12*f*, with the difference that the detector (105, 205, 305) reaches the first turning point before the x-ray source (104, 204, 304). The scan movement is therefore not further explained here.

Figure 15A:
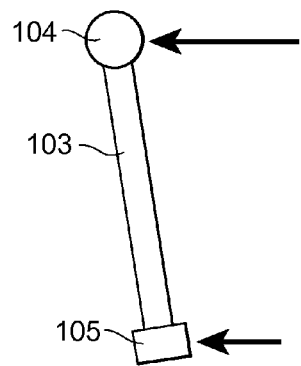
FIG. 15a-15e illustrates a schematic view of the scan arm at certain positions along a scan movement
Figure 15B:
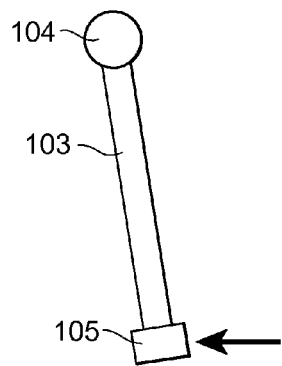
Figure 15C:
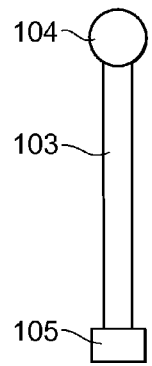
Figure 15D:
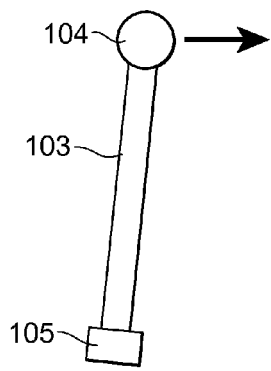
Figure 15E:
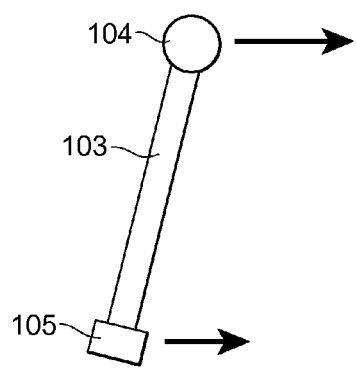
Figure 16A:
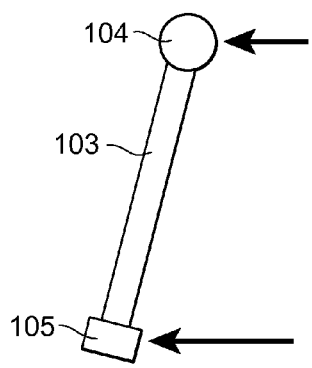
FIG. 16a-16e represents a similar scan movement to that described in FIG. 15a-15f
Figure 16B:
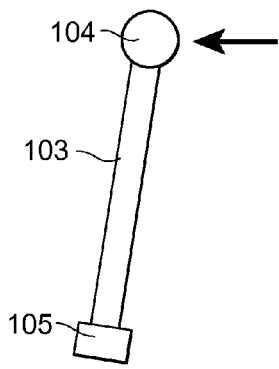
Figure 16C:
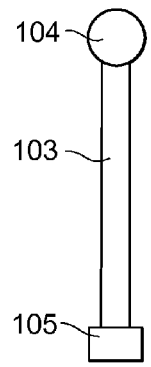
Figure 16D:
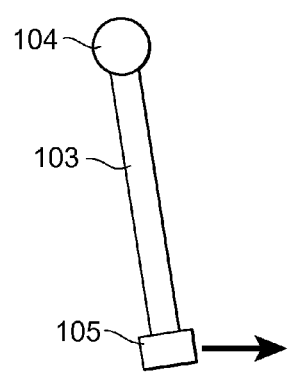
Figure 16E:
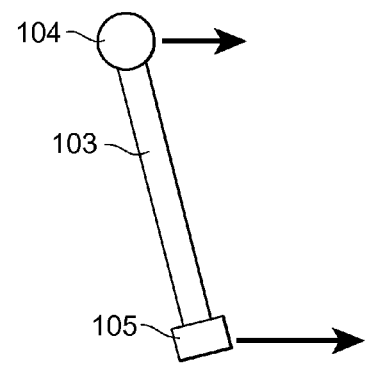

FIG. 15*a*-15*e* illustrates a schematic view of the scan arm (103, 203, 303) comprising an x-ray source (104, 204, 304) and the detector (105, 205, 305) and yet another preferred scan movement wherein a limited 2D scan is performed around the first turning point. FIG. 15*a* shows the x-ray source (104, 204, 304) and the detector (105, 205, 305) moving towards the first turning point. In FIG. 15*b*, the x-ray source (104, 204, 304) has reached the first turning point and stops there wherein the detector (105, 205, 305) continues to move towards its first turning point. FIG. 15*c* shows a position wherein both the x-ray source (104, 204, 304) and the detector (105, 205, 305) has reached their first turning points and wherein a 2D scan has been performed during between the positions of FIGS. 15*b* and 15*c* since no movement of the x-ray source (104, 204, 304) takes place. In FIG. 15*d*, the x-ray source (104, 204, 304) accelerates steeply upon the detector (105, 205, 305) reaching its first turning point. FIG. 15*e* represents a position wherein the detector (105, 205, 305) has started to move towards the second turning point after a certain time.

FIG. 16*a*-16*e* represents a similar scan movement to that described in FIG. 15*a*-15*f*, with the difference that the detector (105, 205, 305) reaches the first turning point before the x-ray source (104, 204, 304). The scan movement is therefore not further explained here.

According to an embodiment of the invention, wherein the control unit is adapted to control the movement of the x-ray source such that tomosynthetic scan movements occur, optimization of tomo-angles is achieved by the control unit controlling the movement of the x-ray source and the detector at every instant in time during a scan movement, wherein a scan of an object occurs. Every adaptation of the speeds and directions of the x-ray source and the detector described herein may be described as an optimization of the tomo-angle, including the high acceleration occurring after the x-ray source or the detector reaches a turning point, wherein external data such as the position of the at least one compression paddle in relation to the detector or collimator, characteristics of the breast such as boundary, thickness, or attenuation resulting from the thickness of the breast sets limitations to achieving the most optimal tomo-angle, i.e. the angle of the scan arm when passing the compression paddle, speed ratio between the x-ray source and the detector, etc.

Figure 17:
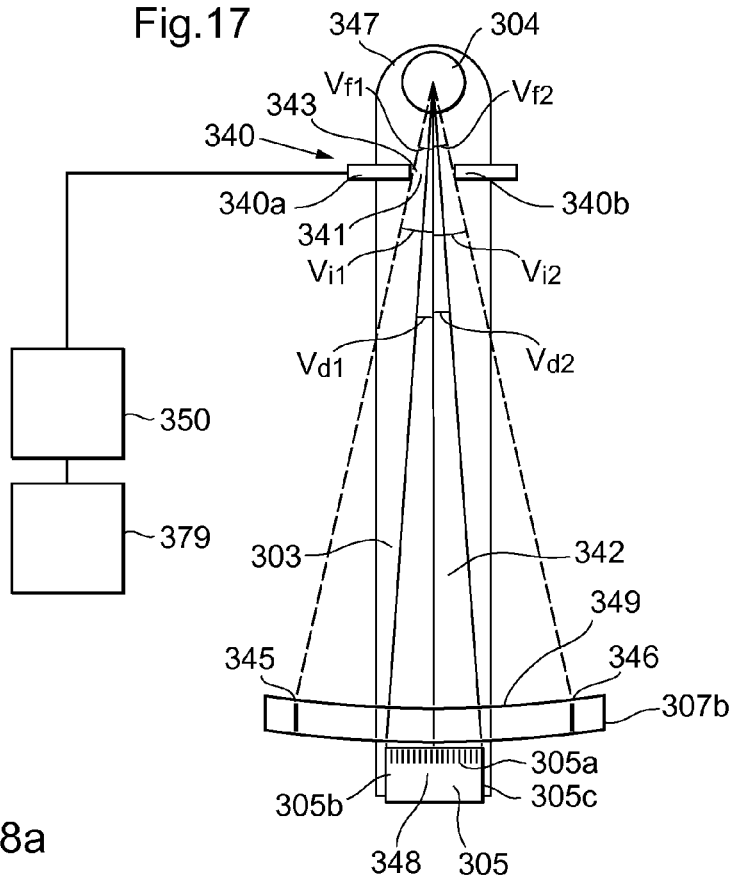
FIG. 17 shows the scan arm with a field limiting device according to one embodiment.

FIG. 17 shows a scan arm 103, 203, 303 and a field limiting device 140, 240, 340 according to one embodiment in a position where the angle of the scan arm 103, 203, 303 in relation to a vertical line is zero. An x-ray source 104, 204, 304 adapted to emit x-ray radiation in an x-ray beam is arranged in a first position 147, 247, 347 of the scan arm 103, 203, 303 corresponding to a first end of the scan arm 103, 203, 303. A detector 105, 205, 305 is arranged in a second position 148, 248, 348 of the scan arm 103, 203, 303 corresponding to a second end of the scan arm 103, 203, 303, and adapted to receive the x-ray beam from the x-ray source. A section of the object 108, 208, 308 table is seen in FIG. 19 comprising an image field 149, 249, 349, having a first end 145, 245, 345 and a second end 146, 246, 346.

The field limiting device 140, 240, 340 comprises at least a portion thereof being arranged essentially between the x-ray source 104, 204, 304 and the detector 105, 205, 305, preferably in a third position of the scan arm 103, 203, 303 at least during certain positions of the field limiting device. The third position of the scan arm corresponds to a position on the scan arm such that a movement of the x-ray source 104, 204, 304 causes a movement of the field limiting device 140, 240, 340. According to another embodiment, the scan arm 103, 203, 303 is not present, wherein no mechanical connection means connect the x-ray source 104, 204, 304, detector and field limiting device but these are adapted to move independently of the movements of each other.

The field limiting device 140, 240, 340 comprises a first side portion 140*a*, 240*a*, 340*a* and a second side portion 140*b*, 240*b*, 340*b* and an opening 141, 241, 341 there between, wherein the x-ray radiation from the x-ray source 104, 204, 304 is allowed to pass through the opening 141, 241, 341 but is blocked by being essentially absorbed by the first 140*a*, 240*a*, 340*a* and second side portion 140*b*, 240*b*, 340*b*. Preferably, the first 140*a*, 240*a*, 340*a* and second side portions 140*b*, 240*b*, 340*b* are made of an x-ray opaque material such as steel and/or lead to increase the absorbing capacity. The first 140*a*, 240*a*, 340*a* and second 140*b*, 240*b*, 340*b* side portions are adapted to be adjustably movable towards a center line of the x-ray radiation field between a first and a second position, wherein the first 140*a*, 240*a*, 340*a* and second 140*b*, 240*b*, 340*b* side portions prevent a larger share of the x-ray radiation from passing the field limiting device 140, 240, 340 in a second position than in a first position. Preferably, the movement of the first 140*a*, 240*a*, 340*a* and second 140*b*, 240*b*, 340*b* side portions is enabled by at least one linear rail upon which the first 140a, 240a, 340a and second side portions 140b, 240b, 340b are adapted to slide. A driving means, preferably an electrical motor drives the first 140a, 240a, 340a and second 140b, 240b, 340b side portions and controls the movement thereof, wherein the electrical motor is controlled by a first control unit 150, 250, 350. The first 140a, 240a, 340a and second 140b, 240b, 340b side portions are adapted to be moved into any position between the first 140a, 240a, 340a and second positions wherein the first 140a, 240a, 340a and second 140b, 240b, 340b side portions prevent a larger share of the x-ray radiation from passing the field limiting device 140, 240, 340 in any such position compared to the first position.

As seen in FIG. 17, the opening 141, 241, 341 of the field limiting device 140, 240, 340 comprises a first angle $v_{f1}$ from the center line 142, 242, 342 of the x-ray beam to the end 143, 243, 343 of the first side portion 140a, 240a, 340a seen from the x-ray source 104, 204, 304, a second angle $v_{f2}$ from a center line 142, 242, 342 of the x-ray beam to the end 144, 244, 344 of the second side portion 140b, 240b, 340b seen from the x-ray source 104, 204, 304. Further, $v_{i2}$ is the angle from a center line 142, 242, 342 of the x-ray beam to the second image end 146, 246, 346 seen from the x-ray source 104, 204, 304, and $v_{i1}$ is the angle from a center line 142, 242, 342 of the x-ray beam to the first image end 145, 245, 345 seen from the x-ray source 104, 204, 304. Angle $v_{d2}$ is defined as the angle from a center line 142, 242, 342 of the x-ray beam to a second end 105c, 205c, 305c of the detector 105, 205, 305 seen from the x-ray source 104, 204, 304, and angle $v_{d1}$ is defined as the angle from a center line 142, 242, 342 of the x-ray beam to a first end 105b, 205b, 305b of the detector 105, 205, 305 seen from the x-ray source 104, 204, 304.

The x-ray source 104, 204, 304 is adapted to be moved in relation to a first portion of the x-ray apparatus 102, 202, 302, and the detector 105, 205, 305 is adapted to be moved in relation to a first portion of the x-ray apparatus 102, 202, 302. In order for the x-ray source 104, 204, 304 and the detector 105, 205, 305 to be in line with each other, i.e. such that an x-ray beam emitted from the x-ray source is received by the detector 105, 205, 305, wherein the x-ray beam is directed essentially towards the detector 105, 205, 305 during the movement of the x-ray source 104, 204, 304 and the detector 105, 205, 305, the x-ray source and the detector 105, 205, 305 are adapted to rotate in relation to first portion of the x-ray apparatus 104, 204, 304. A control unit 121, 221, 321 is adapted for controlling the movement of the x-ray source and the detector. According to one embodiment the control unit is referred to as a second control unit 121, 221, 321. According to another embodiment, the first and second control unit are comprised by the same control unit.

The first portion of the x-ray apparatus is referred to as a fixed portion at any point of the x-ray apparatus, i.e. portion that is essentially non movable, and is thus a fixed position in space.

The second control unit may control the movement of the x-ray source 104, 204, 304 and the detector such that the second control unit 121, 221, 321 is adapted to change direction of the x-ray source 104, 204, 304 and the detector at a first turning point of the x-ray source, and a first turning point of the detector respectively, wherein the x-ray source and the detector move in a second direction after reaching the first turning point which is essentially opposite a first direction prior to reaching the first turning point.

According to one embodiment, the detector comprises a plurality of detector lines, wherein the first control unit is adapted to calculate the angles of the x-ray beam towards each of the detector lines in relation to a vertical line at predefined positions along a path essentially extending in a horizontal direction, based on the position signals from the position sensing arrangement. The first control unit 150, 250, 350 is adapted to save the calculated angles, preferably in a table format in a memory device in the first control unit. Essentially, the saved calculated angles may comprise a list of angles for each millimeter along the path, wherein the path may comprise a straight line along the object table, or a curve at a location within the distance from the object table to a compression paddle depending on scan movement. The first control unit 150, 250, 350 is adapted to control at least the first side portion of the field limiting device to prevent the x-ray beam from being received by the detector lines more than once for each calculated angle at each predefined position along the path essentially extending in a horizontal direction. Since the angles may reoccur due to the change of directions of the x-ray source and the detector at the first turning point, for instance, this is a relevant feature to further reduce the x-ray radiation dose since scanning the same angle twice would not improve the image of the breast, but would be superfluous.

Prior to initiating a scan movement of the x-ray source and the detector, the first control unit may establish the table of calculated angles that will be generated during a main scan movement and the calculated angles that will be generated during a bouncing scan movement occurring at around at least the first turning point. The first control unit 150, 250, 350 may assign binary number 1 for each angle generated during a bouncing scan movement that is generated also during the main scan movement, i.e. wherein there is an overlap, and assign a binary number 0 for each angle generated during a bouncing scan movement that is not generated during the main scan movement. The first control unit is adapted to control at least the first side portion such that it blocks the x-ray beam from radiating detector lines that has been assigned a binary 1 but not a binary 0 during a bouncing scan movement.

According to one embodiment, a main scan movement comprises the movement of the x-ray source 104, 204, 304 and the detector before the x-ray source reaches the first turning point and after the detector reaches the first turning point.

According to one embodiment, the bouncing scan movement comprises the movement of the x-ray source 104, 204, 304 and the detector from when the x-ray source reaches the first turning point until the detector reaches the first turning point, or, alternatively, from when the x-ray source 104, 204, 304 reaches the first turning point, the detector reaches the first turning point, and until the x-ray source 104, 204, 304 reaches a second turning point wherein the x-ray source 104, 204, 304 changes direction of movement again, essentially moving in the first direction.

According to one embodiment, the first control unit is adapted to control the movement of at least the first side portion during a CC-scan, also known as Cranio caudial scan, wherein only a specific portion a breast is scanned, such as to limit the size of the image field during the scan movement by the size of the opening between the first and second side portions, wherein radiation of an x-ray beam is prevented outside the image field during such scan movement. Another type of scan wherein such limitation of the image field by the controlling of at least the first side portion is the MLO-scan, Medial lateral oblique scan movement.

Figure 18A:
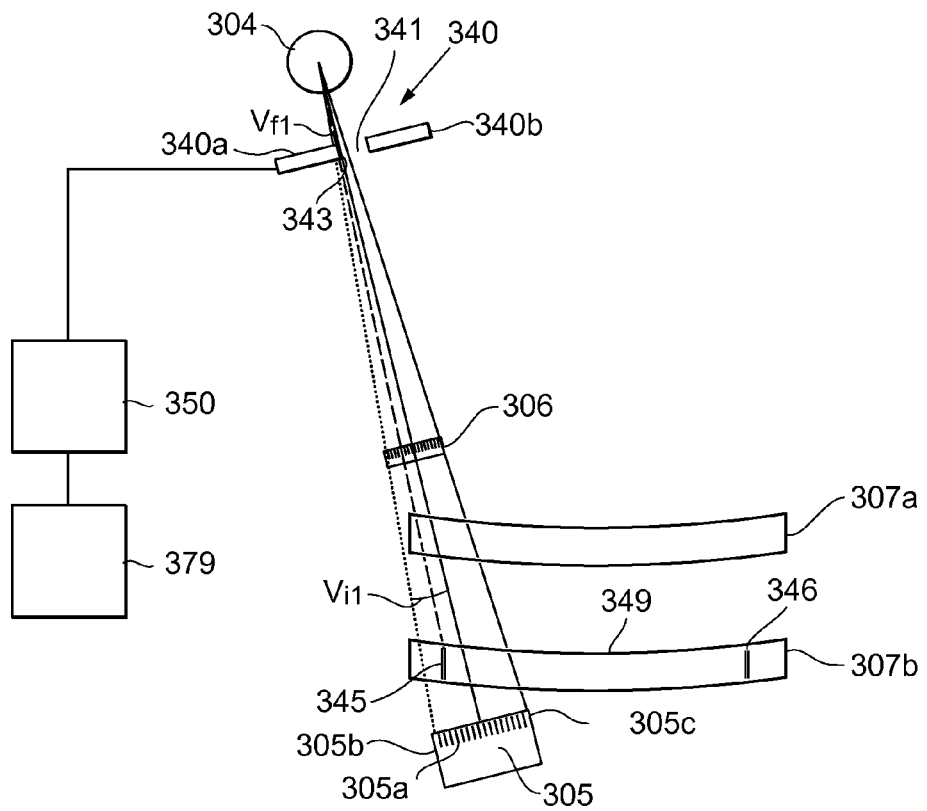
FIG. 18a shows the scan arm with a field limiting device according to a one embodiment wherein a first portion of the field limiting device prevents radiation outside a first image end.

FIG. 18a shows the scan arm 103, 203, 303 with a field limiting device 140, 240, 340 according to a one embodiment wherein the x-ray source 104, 204, 304 has moved along an arbitrary first movement path, and the detector 105, 205, 305 has moved, for instance along a arbitrary second movement path towards the first turning points in the first and second movement paths, into a position such that $v_{d1}$ is larger than $v_{i1}$, or in other words, such that the x-ray beam extends outside the first image field 149, 249, 349 provided that no field limiting device 140, 240, 340 is used. Naturally, such x-ray beam radiation does not contribute to enhancing the mammographic images and an object 108, 208, 308 is therefore to reduce such radiation. As disclosed in FIG. 18*a*, the first side portion 140*a*, 240*a*, 340*a* has moved slightly towards a second position in order to prevent x-ray radiation from irradiating an area outside the first image end 145, 245, 345. The first control unit 150, 250, 350 is adapted to control the movement of the first 140*a*, 240*a*, 340*a* and second side portion 140*b*, 240*b*, 340*b* based on data stored in a memory means of the control unit 150, 250, 350, the data comprising information regarding the necessary positions of the first 140*a*, 240*a*, 340*a* and second side portions 140*b*, 240*b*, 340*b* based on the positions of the x-ray source 104, 204, 304 and the detector 105, 205, 305. In order to sense the positions of the x-ray source and the detector, a position sensing arrangement is provided as described herein, comprising any or all of first position sensing device 173, 273, 373, second position sensing device 172, 272, 372, third position sensing device 178, 278, 378, fourth position sensing device 171, 271, 371, fifth position sensing device 170, 270, 370, sixth position sensing device 180, 280, 380 or combination thereof. Any other type of position sensing device may be used that in a direct or indirect manner is able to sense or deduce the positions of the x-ray source 104, 204, 304 and the detector 105, 205, 305.

The first control unit is further adapted for receiving the position signals from the position sensing arrangement wherein the first control unit is adapted to control the movement of at least the first side portion based on the position signals. According to one embodiment, the first control unit may be equal to the recording device 179, 279, 379.

Figure 18B:
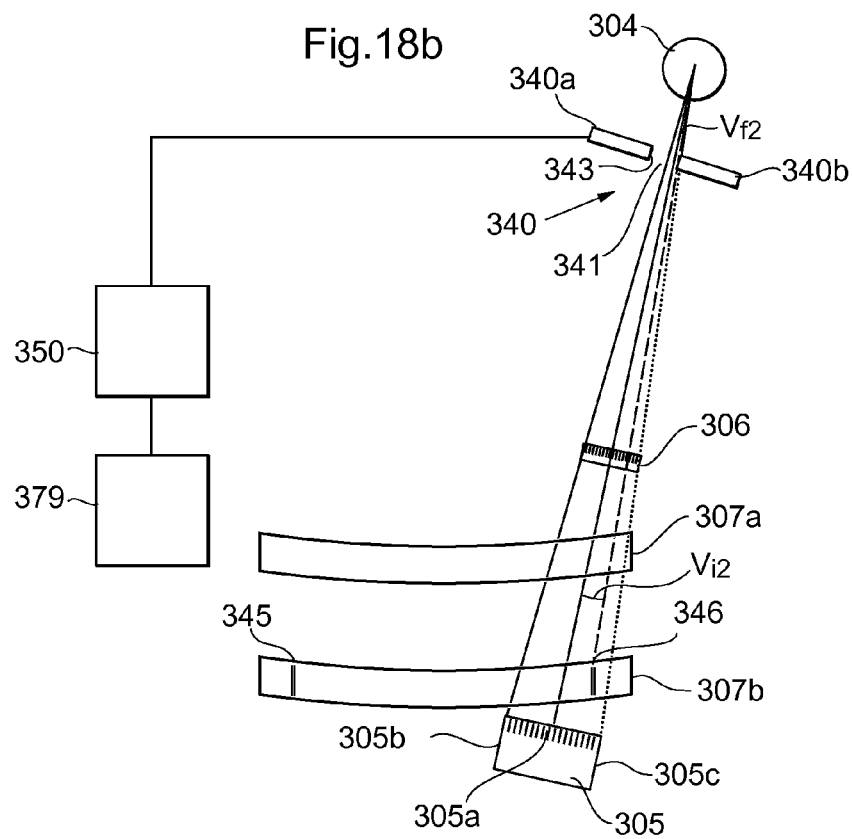
FIG. 18b shows the scan arm with a field limiting device according to one embodiment wherein the field limiting device prevents radiation outside a second image end.

In an analogous manner, as seen in FIG. 18*b*, the second side portion 140*b*, 240*b*, 340*b* is adapted to move towards a second position in order to prevent x-ray radiation from irradiating an area outside the second image end 146, 246, 346.

Figure 18C:
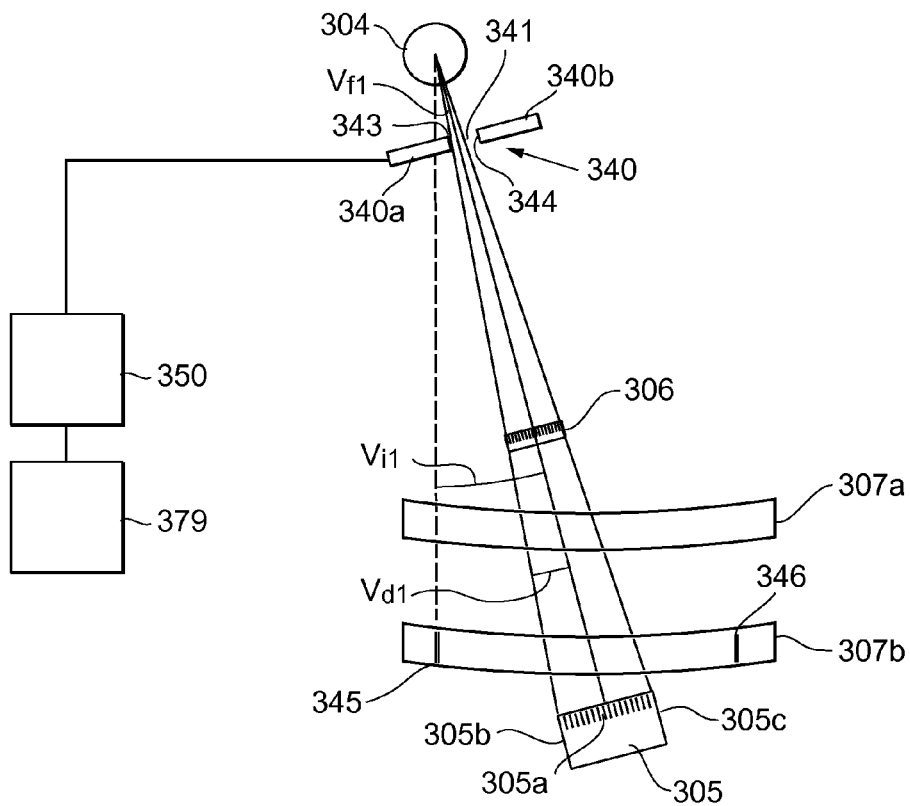
FIG. 18c shows the scan arm with a field limiting device according to one embodiment wherein the field limiting device prevents radiation outside a first end of the detector.
Figure 18D:
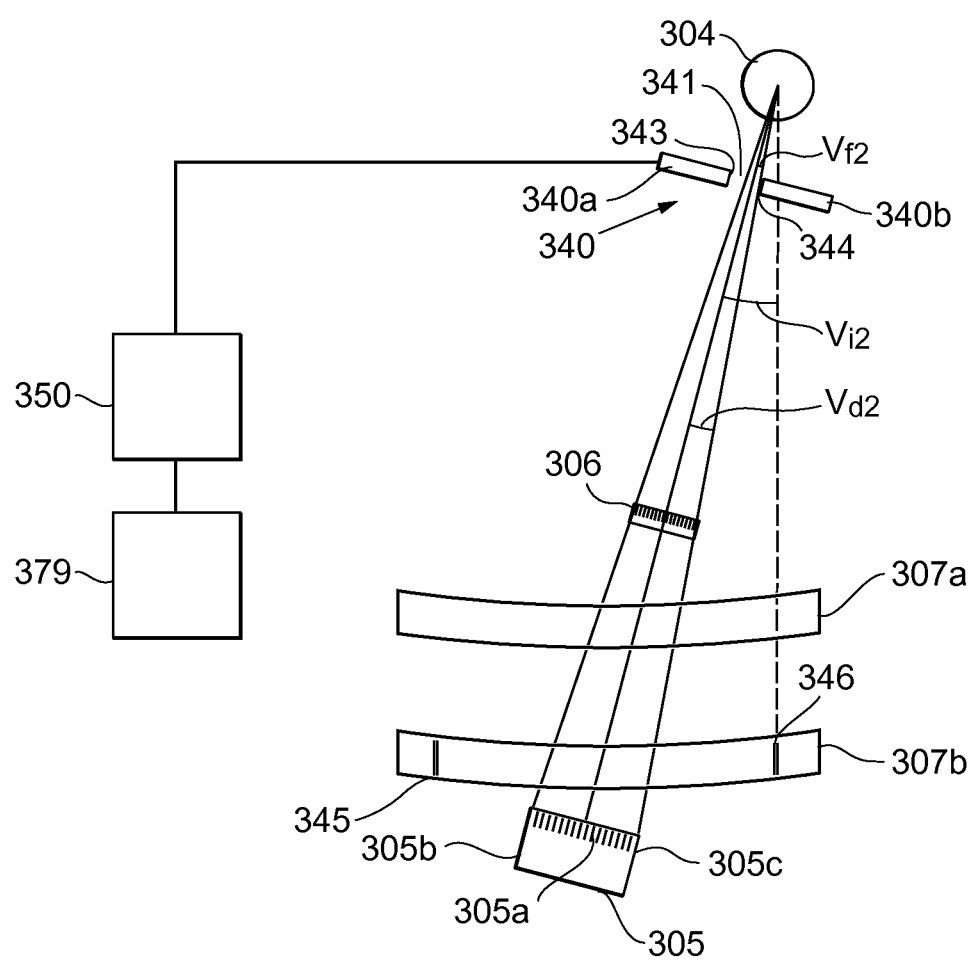
FIG. 18d shows the scan arm with a field limiting device according to one embodiment wherein the field limiting device prevents radiation outside a second end of the detector.

FIG. 18*c* discloses the scan arm 103, 203, 303 with a field limiting device 140, 240, 340 according to one embodiment wherein the x-ray source 104, 204, 304 and the detector 105, 205, 305 have moved along their movement paths towards a first turning point into a position such that $v_{d1}$ is smaller than $v_{i1}$, or in other words, such that the x-ray radiation field extends outside the first detector end 105*b*, 205*b*, 305*b* provided that no field limiting device 140, 240, 340 is used. As in the case of FIG. 18*a*, such radiation would not contribute to enhancing the mammographic images and must be blocked. Therefore, as seen in FIG. 18*c*, the first side portion 140*a*, 240*a*, 340*a* has moved towards a second position in order to prevent x-ray radiation from irradiating an area outside the first detector end 105*b*, 205*b*, 305*b*. In an analogous manner, as seen in FIG. 18*d*, the second side portion 140*b*, 240*b*, 340*b* is adapted to move towards a second position in order to prevent x-ray radiation from irradiating an area outside the second detector end 105*c*, 205*c*, 305*c*.

Thus, concluding the synchronized field limiting device 140, 240, 340 movements of FIG. 18*a*-FIG. 18*d*, the first control unit 150, 250, 350 is adapted to control the movement of the first side portion 140*a*, 240*a*, 340*a* if $v_{i1} < v_{d1}$ such that $v_{f1} \leq v_{i1}$, if $v_{i1} > v_{d1}$ such that $v_{f1} \leq v_{d1}$ and the movement of the second side portion 140*b*, 240*b*, 340*b* if $v_{i2} < v_{d2}$ such that $v_{f2} \leq v_{i2}$, if $v_{i2} > v_{d2}$ such that $v_{f2} \leq v_{d2}$.

Naturally, the first 140*a*, 240*a*, 340*a* and second side portions 140*b*, 240*b*, 340*b* are adapted to move between the first 140*a*, 240*a*, 340*a* and second positions based on a movement of the x-ray source 104, 204, 304 and the detector 105, 205, 305, and the direction of the movement of the side portions are related to the movement direction of x-ray source 104, 204, 304 and the detector 105, 205, 305. Thus, the first side portion 140*a*, 240*a*, 340*a* is adapted to move towards the second position if $v_{i1}$ is decreasing, and adapted to move towards the first position if $v_{i1}$ is increasing. The second side portion 140*b*, 240*b*, 340*b* is hence adapted to move towards a second position if $v_{i2}$ is decreasing and towards a first position if $v_{i2}$ is increasing.

FIG. 19*a* discloses another embodiment of the scan arm 103, 203, 303 with a field limiting device 140, 240, 340 wherein the field limiting device 140, 240, 340 comprises a cylindrical device 151, 251, 351 having an aperture, wherein the portion of the cylindrical device 151, 251, 351 defining a first end of the aperture comprises a first side portion 140*a*, 240*a*, 340*a*, and the portion of the cylindrical device 151, 251, 351 defining a second end of the aperture comprises the second side portion 140*b*, 240*b*, 340*b*. The cylindrical field limiting device 140, 240, 340 is pivotally arranged for rotation around the x-ray source 104, 204, 304.

The first control unit 150, 250, 350 is adapted to rotate the cylindrical device 151, 251, 351 based on the positions of the x-ray source 104, 204, 304 and the detector 105, 205, 305, for instance along their first 140*a*, 240*a*, 340*a* and second movement paths in an analogous manner to the embodiment described in FIGS. 17-19, and wherein the references to angles are identical. The position of the x-ray source 104, 204, 304 and the detector 105, 205, 305 as seen in FIG. 19*a* results in a relationship between the angles such that $v_{i2} < v_{f2}$, before rotation of the field limiting device 140, 240, 340, wherein, as a result, the cylindrical device 151, 251, 351 is adapted to rotate an angle $v_{rot2} = (v_{f2} - v_{i2})$ resulting in a movement of the first 140*a*, 240*a*, 340*a* and second end of the aperture moving towards a second position, to prevent x-ray radiation from irradiating an area outside the second image end 146, 246, 346. In an analogous manner, as seen in FIG. 19*b*, the cylindrical device 151, 251, 351 is adapted to rotate towards a second position $v_{rot1} = (v_{f1} - v_{i1})$, if $v_{i1} < v_{f1}$, in order to prevent x-ray radiation from irradiating an area outside the first image end 145, 245, 345.

It should be noted that, according to one embodiment, the second side portion 140*b*, 240*b*, 340*b* is adapted to move towards a first position, a second position or not move, as the first side portion 140*a*, 240*a*, 340*a* moves towards the second position, wherein the second side portion 140*b*, 240*b*, 340*b* prevents a larger share of the x-ray radiation from passing the field limiting device 140, 240, 340 in a second position than in a first position.

FIG. 20 illustrates schematically an x-ray imaging system 101, 201, 301 according to one embodiment, wherein the system comprises an x-ray apparatus 102, 202, 302. The x-ray apparatus 102, 202, 302 comprises a scan arm 103, 203, 303, wherein an x-ray source 104, 204, 304 is arranged on one upper end of the scan arm but may be arranged at any position along the scan arm 103, 203, 303 according to other embodiments of the invention. A detector is arranged in the other 105, 205, 305, lower end of the scan arm 103, 203, 303, wherein the detector comprises a plurality of detector strips 105*a*, 205*a*, 305*a*, each detector strip built up by a plurality of detector pixels. The detector 105, 205, 305 may however be arranged at any position along a scan arm 103, 203, 303 according to other embodiments of the invention. A collimator 106, 206, 306 comprising a plurality of slits is arranged between the x-ray source and the detector on the scan arm 103, 203, 303.

FIG. 20 further shows a schematic view of the x-ray apparatus 102, 202, 302, wherein the arrangement and parts of the apparatus that enables both 2D scan motions and 3D scan motions are further explained. As seen in the figure, in a position slightly below the x-ray source 104, 204, 304, the scan arm is pivotally arranged in a first end of a first suspension arm 109, 209, 309. The pivot point may be arranged in the center of the x-ray source 104, 204, 304, and the first end 109a, 209a, 309a of the first suspension arm 109, 209, 309 may be pivotally arranged in an upper x-ray source portion 104a, 204a, 304a.

As seen in FIG. 21, the second end 109b, 209b, 309b of the first suspension arm 109, 209, 309 is arranged linearly displaceable in relation to a first end 110a, 210a, 310a of a second suspension arm 110, 210, 310, in a manner such that the total length of the first 109, 209, 309 and second suspension arm 110, 210, 310 may be varied. According to one embodiment, the first suspension arm 109, 209, 309 is arranged partly inside the second suspension arm 110, 210, 310, however the arrangement may be the other way around, i.e. wherein the second suspension arm 110, 210, 310 is partly arranged inside the first suspension arm 109, 209, 309. A motor 177, 277, 377 is adapted to a the linear screw 115, 215, 315 arrangement and thereby actuate the linear displacement of the first and suspension arms. Further, the second end 110b, 210b, 310b of the second suspension arm 110, 210, 310 is pivotally arranged in a lower portion 111, 211, 311 of the x-ray apparatus.

FIG. 22 shows a side view of the x-ray apparatus. In order to control the rotational movement of the scan arm 103, 203, 303 in relation to the first suspension arm 109, 209, 309, a first motor 116, 216, 316, preferably of electrical kind, is arranged, preferably on the first suspension arm 109, 209, 309, wherein a first sprocket 117, 217, 317 is adapted to be rotated upon the activation of the first motor 116, 216, 316 in one of two rotational directions. A second sprocket 118, 218, 318, preferably larger than the first sprocket 117, 217, 317, is arranged on the scan arm 103, 203, 303 in order to be engaged by the first sprocket 117, 217, 317, wherein a rotational movement of the first sprocket 117, 217, 317 is transferred to generate a rotational movement of the second sprocket 118, 218, 318 and the scan arm 103, 203, 303. The second sprocket 118, 218, 318 is arranged on a pivot axis 175, 275, 375, adapted to be rotated in relation to the first suspension arm 109, 209, 309 and extends through the first suspension arm 109, 209, 309. At one end of the pivot axis 175, 275, 375, a first position sensing device 173, 273, 373 is arranged. The first position sensing device 173, 273, 373 comprises a first rotary position encoder 173, 273, 373. The first rotary position encoder 173, 273, 373 comprises a rotary portion 173b, 273b, 373b arranged on an end of the pivot axis 175, 275, 375, and a sensing portion 173a, 273a, 373a arranged on the first suspension arm 109, 209, 309, wherein the sensing portion 173a, 273a, 373a is adapted to sense the relative rotational position of the rotary portion 173b, 273b, 373b and hence the actual relative rotational position of the scan arm 103, 203, 303 in relation to the first suspension arm 109, 209, 309.

A second motor 126, 226, 326, preferably an electrical motor and similar to the first motor 116, 216, 316, is arranged in the lower portion 111, 211, 311 or in another part of the x-ray apparatus 102, 202, 302, wherein a third sprocket 120, 220, 320 is arranged to be rotated upon the activation of the motor in one of two rotational directions. A fourth sprocket 120, 220, 320, preferably larger than the third sprocket 119, 219, 319, is arranged on the second suspension arm 110, 210, 310 in order to be engaged with the third sprocket 119, 219, 319, wherein a rotational movement of the third sprocket 119, 219, 319 is transferred to generate a rotational movement of the fourth sprocket 120, 220, 320 and the second suspension arm 110, 210, 310. The fourth sprocket 120, 220, 320 is arranged on a pivot axis 174, 274, 374, adapted to be rotated in relation to the lower portion 111, 211, 311 and extends through the lower portion 111, 211, 311. At one end of the pivot axis 174, 274, 374, a second position sensing device 172, 272, 372 is arranged. The second position sensing device 172, 272, 372 comprises a second rotary position encoder 172, 272, 372. The second rotary position encoder 172, 272, 372 comprises a rotary portion 172b, 272b, 372b arranged on an end of the pivot axis 174, 274, 374, and a sensing portion 173a, 273a, 373a arranged on the lower portion 111, 211, 311, wherein the sensing portion 173a, 273a, 373a is adapted to sense the relative rotational position of the rotary portion 173b, 273b, 373b and hence the actual relative rotational position of the second suspension arm 110, 210, 310 in relation to the lower portion 111, 211, 311.

A third position sensing device 178, 278, 378 comprising a linear position encoder 178, 278, 378 is adapted to sense the actual relative linear position between the second end 109b, 209b, 309b of the first suspension arm 109, 209, 309 and the first end 210a, 210a, 310a of the second suspension arm 110, 210, 310, and hence the total length of the first and second suspension arms. The linear position encoder 178, 278, 378 comprises a position sensor 178a, 278a, 378a arranged on either of the first or the second suspension arm, and a scale for a position sensor is arranged on the other of the first or second suspension arm.

A fourth position sensing device 171, 271, 371 is adapted to sense the relative rotational position of a rotor 116a, 216a, 316a of the first motor 116, 216, 316 and the motor casing 116b, 216b, 316b, wherein the set relative rotational position of the scan arm 103, 203, 303 and the first suspension arm 109, 209, 309 is sensed. Hence, the fourth position sensing device comprises a third rotary position encoder 171, 271, 371.

A fifth position sensing device 172, 272, 372 is adapted to sense the relative rotational position of a rotor 126a, 226a, 326a of the second motor 126, 226, 326 and the motor casing 126b, 226b, 326b, wherein the set relative rotational position of second suspension arm 110, 210, 310 and lower portion 111, 211, 311 is sensed. Hence, the fifth position sensing device comprises a fourth rotary position encoder 172, 272, 372.

A sixth position sensing device 180, 280, 380 is adapted to sense the relative rotational position of a rotor of the third motor 177, 277, 377 and the motor casing 177b, 277b, 377b, wherein the set relative linear position of the first suspension arm 209, 209, 309 and the second suspension arm 110, 210, 310 is sensed by first transforming this data with regard to the screw pitch of the third linear screw 115, 215, 315. Hence, the sixth position sensing device comprises a fifth rotary position encoder 180, 280, 380.

A control unit 121, 221, 321 is connected to the motors 116, 216, 316, 126, 226, 326, 177, 277, 377 in order to control the motors and thereby the rotational movement of the first 109, 209, 309 and second 110, 210, 310 suspension arms, and the scan arm 103, 203, 303, as well as the length of the first and second suspension arms. By means of this arrangement, arbitrary movement in two dimensions of the x-ray source 104, 204, 304 and the detector 105, 205, 305 is enabled within the mechanical restraints of the rotational limits between the scan arm 103, 203, 303 and the first suspension arm 109, 209, 309, the varying of the total length of the first and second 110, 210, 310 suspension arm, and the connection between the x-ray source 104, 204, 304 and the detector 105, 205, 305 through the scan arm 103, 203, 303. In the embodiment wherein a scan arm 103, 203, 303 is not present, an additional degree of freedom in the relative movement between the x-ray source 104, 204, 304 and the detector 105, 205, 305 is present. When the detector 105, 205, 305 and x-ray source 104, 204, 304 are connected by a scan arm 103, 203, 303, an x-ray beam 122, 222, 322 irradiated from the x-ray source 104, 204, 304 is thus set to be directed towards, and irradiate, the detector 105, 205, 305. In any embodiment wherein no scan arm 103, 203, 303 is present, and the absolute distance between the x-ray source 104, 204, 304 and the detector 105, 205, 305 may vary, a control unit 121, 221, 321 is adapted to rotate the x-ray source 104, 204, 304 and the detector 105, 205, 305 such that radiation from the x-ray source 104, 204, 304 is adapted to be directed towards, and irradiate the detector 105, 205, 305.

During the scan movement of the x-ray source 104, 204, 304 and the detector 105, 205, 305 in relation to an object, the x-ray source 104, 204, 304 may thus be moved along an arbitrary first movement path that is redefined at any instant in time and between different scans as well as being rotated during this movement. In a similar manner, the detector 105, 205, 305 may be moved along an arbitrary second movement path that is redefined at any instant in time and between different scans, as well as being rotated during this movement. Further, a scan movement may be referred to as the movement of the x-ray source 104, 204, 304 and/or the detector 105, 205, 305 along a first and a second movement path. The scan movement further comprises a subset movement when the irradiated x-rays are actually impinging on an object 108, 208, 308 wherein an image of the object can be reconstructed. Such movement is hereinafter referred to as a scan of an object.

The x-ray apparatus 102, 202, 302 further comprises a position sensing arrangement adapted for sensing positions corresponding to the positions of the x-ray source and the detector and transmitting the position signals the positions of the x-ray source and detector. According one embodiment, the position sensing arrangement is adapted for sensing positions corresponding to the positions of the x-ray source and the detector during their movements along the first and second movement paths respectively.

The position sensing arrangement of the x-ray apparatus comprises any or all of the first position sensing device 173, 273, 373, second position sensing device 172, 272, 372, third position sensing device 171, 271, 371, fourth position sensing device 172, 272, 372, fifth position sensing device 178, 278, 378, sixth position sensing device 180, 280, 380 or a combination thereof. Each of the first to sixth position sensing devices is adapted to emit signals corresponding to the sensed relative positions. Further, each of the first to sixth position sensing devices is connected to a recording device 179, 279, 379, via a second connection device 184, 284, 384 wherein the recording device 179, 279, 379 is adapted to receive and record said position signals corresponding to the relative positions.

According to another embodiment, any type of position sensing device may be used for either sensing the actual positions corresponding to the positions of the x-ray source and the detector or the set positions corresponding to the positions of the x-ray source and the detector. Such position sensing devices may comprise devices adapted to sense relative rotational positions that need to be transformed into actual positions, or positions directly sensing the coordinates of the x-ray source and the detector.

During a scan movement, the recording device 179, 279, 379 is adapted to record signals corresponding to the relative positions of the position sensing arrangement, i.e. the entire movement may be recorded in said recording device, regardless if the movements correspond to a 2D scan or a 3D scan or any other type of scan movement.

Further, during the scan movement, especially during a scan of an object, readout of data from the detector concerning the amount of photons impinging the detector pixels of each detector strip occurs in a frequent manner in order to acquire the necessary amount of data for each projection angle of the x-ray source and detector in relation to the object, necessary for the reconstruction of the image. Read out data is transmitted to an image reconstruction device via a first connection device 183, 283, 383, wherein the image reconstruction device is implementing back projection algorithms, wherein during reconstruction of the tomosynthesis images or other image types the positions of the x-ray source and the detector for every readout by the detector is taken into account. The image reconstruction device is connected to the recording device via a third connection device 185, 285, 385, wherein signals from the recording device can be transmitted from the recording device to the image reconstruction device. The recording device or the image reconstruction device, or any other device in the x-ray apparatus may be adapted to deduce the actual positions of the x-ray source and the detector from the signals of the position sensing arrangement which correspond to the sensed relative positions. Hence, either one of the recording device and the image reconstruction device or any other device in the x-ray apparatus thus comprises information such as e.g. the length distance between the x-ray source and the detector, the position of the pivot point of along the scan arm, etc. which is necessary for transformation of relative position signals into actual positions or coordinates of the x-ray source and the detector, as well as means for transforming the relative position signals into the actual position signals of the x-ray source and the detector.

By including the actual positions of the x-ray source and the detector in the tomosynthesis reconstruction process, the detector readout images can be optimized in terms of reduced motion blur effects. Data concerning the reconstructed tomosynthesis images or other images are sent to a display device 182, 282, 382, wherein the images can be reviewed and analyzed, for instance by an operator of the system in order to identify for instance abnormalities in a breast or other parts of the human body.

According to one embodiment, each of the first, second and third connection devices is one of a signal cable or a transmitter for wireless communication.

According to one embodiment, readout of data is performed upon the position signals from at least one of the fourth, fifth or sixth position sensors related to the positions of the motors, corresponding to predefined positions for instance defined in the control unit 121, 221, 321 for controlling the movement of the motors. The scan movement is recorded by the recording device by recording signals from the position sensing arrangement.

According to one embodiment, readout of data from the detector is performed at certain predefined points in time.

According to one embodiment, readout of data is performed upon the position signals of at least one of the first, second, and third position sensing devices, related to for instance the relative positions of the scan arm, the first and second suspension arms, the relative position of the second suspension arm and a lower portion of the x-ray apparatus, corresponding to predefined positions. The scan movement is recorded by the recording device by recording signals from the position sensing arrangement.

Whenever the signals from the third, fourth or sixth position sensing device of the position sensing arrangement is recorded by the recording device for recording the scan movement, an alteration or transformation of the signals needs to be performed before the image reconstruction step in order to take into account the play that may be built into the system that causes motion blur. Hence, with knowledge of the exact positions that corresponds to a certain motor position, i.e. the built-in play in the system for such motor positions, the data can be adjusted before the image reconstruction step. Such information may be retrieved by a system such as the herein described, through a calibration step at the assembly line during production of the apparatus, wherein the exact position signals are recorded from at least one of the first, second and third position sensing devices parallel to the recording signals from the fourth, fifth and sixth position sensing devices of the motors. In this manner, a calibration tool may be generated wherein exact positions related to every motor position are saved into the system in a memory device for instance comprised in the recording device or the image reconstruction device.

According to one embodiment, the method comprises the following steps:
1. Start X-ray source, start a scan motion,
2. Repeat until exposure stops:
    wait until one position encoder reaches a target position, as defined in a table,
    readout X-ray detector and store value, and simultaneously readout all other position encoders and store values
    lookup next target position, using said table.
3. Exposure off, stop scan motion
4. Apply gray-level correction of all data, determine number of slices to reconstruct and at what coordinates
5. For each voxel position, in the volume to reconstruct, determine corresponding coordinate in the stored detector signals. (An optimization, it may be enough to store coordinates along the scan direction)
The coordinates are determined by mapping a straight line from the X-ray source position, through the voxel's location in real world space, and towards unto a projection images. This operation involves geometry according to any person skilled in the art of geometry, wherein the X-ray source position is calculated by looking up the corresponding recorded positions, and calculating a coordinate in the projection image data, based on a samples of recorded data. This lookup involves computing an inverse of a sampled function. Methods may be iterative gradient descent/inverse interpolation.
(Geometric calculations involves dimensions of mechanical parts in the apparatus, some of which may be pre-calibrated by scanning a known object with a set of sharp edges.)
6. Preferably, we also compute inverse of the local coordinate transformations, i.e. compute each projection image pixel's coordinates in the voxel to reconstruct.
7. Reconstruct image, using back projection, or preferably iterative reconstruction algorithm, involving back projection and its inverse, and back projection again, etc. This step relies on resampling projection images, or filtered/processed versions thereof, wherein the resampling uses the computed coordinate transformations.
8. Display image or a slice thereof, or send the image volume to an archive, commonly known as PACS.

The invention claimed is:
1. An x-ray apparatus comprising:
an x-ray source adapted to emit an x-ray beam,
a detector adapted to receive the x-ray beam of the x-ray source,
wherein the x-ray source is adapted to be moved in relation to a first portion of the x-ray apparatus,
wherein the detector is adapted to be moved in relation to a first portion of the x-ray apparatus,
the x-ray apparatus further comprising a control unit for controlling the movement of the x-ray source and detector,
wherein the x-ray source and the detector are adapted to rotate in relation to a first portion of the x-ray apparatus,
wherein further the x-ray beam is directed essentially towards the detector during the movement of the x-ray source and the detector,
wherein the control unit is adapted to receive external data,
wherein the control unit is further adapted to control the movement of the x-ray source and the detector based on external data,
wherein the x-ray apparatus further comprises at least one position adjustable compression paddle, and a means for determining the position of the at least one compression paddle adapted to output paddle position data corresponding to the position of the at least one compression paddle,
wherein the external data, which is received by the control unit, comprises paddle position data, and
wherein the control unit is adapted to control a scan movement and/or the remainder of a scan movement of the x-ray source and the detector based on the external data, such that a tomosynthetic scan movement is performed, wherein tomographic projection angles of an object placed in the x-ray beam are optimized based on the external data.
2. An x-ray apparatus according to claim 1, wherein the detector is adapted to sense characteristics of an x-ray beam in real time during a scan movement, wherein the detector is further adapted to output x-ray beam data corresponding to characteristics of the x-ray beam, and wherein the external data, which is received by the control unit for controlling the remainder of the scan movement of the x-ray source and the detector, comprises x-ray beam data.
3. An x-ray apparatus according to claim 1, wherein the detector is adapted to receive impinging photons from the x-ray source during a scan movement, the detector further being adapted to detect an x-ray intensity based on the rate of impinging photons, wherein the control unit is further adapted to receive external data from the detector that a scan of an object placed in the x-ray beam is initiated by detecting a lower intensity, as an object to be scanned starts attenuating photons from the x-ray beam.
4. An x-ray apparatus according to claim 3, wherein the control unit is adapted to control the movement of x-ray source and the detector such that a speed of at least the x-ray source decreases as the first end of the detector senses a decreased count rate at least during the scan of the object.
5. An x-ray apparatus according to claim 3, wherein a first detected x-ray intensity decreases a speed of at least the x-ray source to a first velocity, a second detected x-ray intensity decreases the speed of the x-ray source to a second velocity, wherein, if the first detected x-ray intensity is lower than the second detected x-ray intensity, the first velocity is lower than the second velocity at least during a scan of the object.

6. An x-ray apparatus according to claim 1, wherein the control unit is adapted to control a speed of the detector such that the speed of the detector is lower than a speed of the x-ray source at least during a scan of an object.

7. An x-ray apparatus according to claim 5, wherein the control unit is adapted to control the speed of the x-ray source and the detector such that a ratio between the speed of the x-ray source and the detector is lower for a lower detected x-ray intensity compared to a higher detected x-ray intensity during a scan of the object and/or compared between two separate scan of objects.

8. An x-ray apparatus according to claim 6, wherein the control unit is adapted to control the speed of the x-ray source and the detector such that the ratio is high enough to allow the x-ray source to pass the detector in a horizontal direction during the movement of the x-ray source and the detector, wherein the count rate corresponds to the object being scanned.

9. An x-ray apparatus according to claim 3, wherein the control unit is adapted to control a speed of at least the x-ray source based on the position of the at least one compression paddle during a scan of the object such that a first position of the at least one compression paddle sets the speed of at least the x-ray source to a first velocity, a second position of the at least one compression paddle sets the speed of at least the x-ray source to a second velocity, wherein, if the first position of the at least one compression paddle is higher in a vertical direction than the second position of the at least one compression paddle, the first velocity is lower than the second velocity.

10. An x-ray apparatus according to claim 9, wherein the control unit is adapted to control the speed of the x-ray source and a speed of the detector such that a ratio between the speeds of the x-ray source and the detector is lower for a higher position of the compression paddle compared to a lower position of the compression paddle at least during a scan of the object.

11. An x-ray apparatus according to claim 9, wherein the control unit is adapted to control the speeds of the x-ray source and the detector such that the ratio is high enough to allow the x-ray source to pass the detector in a horizontal direction at least during a scan of the object.

12. An x-ray apparatus according to claim 3, wherein the control unit is adapted to control the movement of the x-ray source and the detector such that a straight line between the x-ray source and a center of the detector in relation to a vertical line essentially extending through a first portion of the x-ray apparatus defines an angle ($\alpha$) wherein the detector moves before the x-ray source towards the object to be scanned, wherein the angle ($\alpha$) is set during a start of a movement of the x-ray source and the detector until scan of an object is initiated, wherein the angle ($\alpha$) decreases with the position of the at least one compression paddle.

13. An x-ray apparatus according to claim 12 wherein the control unit is adapted to control the speeds of the x-ray source and the detector such that the ratio there between is high enough so that the angle ($\alpha$) has a first value, passes zero degrees and has a second value at the end of the scan of an object, wherein the first and second values essentially maximized under constraint of avoiding collision with a compression paddle.

14. An x-ray apparatus according to claim 12, wherein the control unit is adapted to control the angle ($\alpha$) such that the spread of local tomographic projection angles remains constant during the entire scan movement.

15. An x-ray apparatus according to claim 12, wherein the control unit is adapted to control the movement of the x-ray source and the detector such that the angle ($\alpha$) does not exceed a limit value, wherein the limit value is continuously varying with the position of the x-ray source and the positions of the detector, and furthermore depends on the position and type of the compression paddle.

16. An x-ray apparatus according to claim 12, wherein the limit value of angle ($\alpha$) depends on the position of the at least one compression paddle.

17. An x-ray apparatus according to claim 15, wherein the apparatus comprises two compression paddles, wherein an object can be compressed between said two compression paddles, wherein the limit value of angle ($\alpha$) decreases if the distance between the compression paddles increases.

18. An x-ray apparatus according to claim 1, further comprising a scan arm, wherein the x-ray source is arranged at a first position on the scan arm and the detector is arranged at a second position on the scan arm.

19. An x-ray apparatus according to claim 18, wherein the first position of the scan arm corresponds to a first end of the scan arm and the second position of the scan arm corresponds to a second end of the scan arm.

20. An x-ray apparatus according to claim 18, wherein the scan arm further comprises a multi-slit collimator arranged between the x-ray source and the detector on the scan arm, wherein the control unit is adapted to control the movement of the x-ray source and the detector such that a collision between the at least on compression paddle and the collimator is prevented.

21. An x-ray apparatus according to claim 1, wherein the control unit is adapted to change direction of the x-ray source and/or the detector at a first turning point for the x-ray source and at a first turning point for the detector respectively, wherein the x-ray source either moves in a second direction or stops after reaching the first turning point and the detector either moves in a second direction or stops after reaching the first turning point, and wherein the second directions are essentially opposite the first directions before reaching the first turning points.

22. An x-ray apparatus according to claim 21, wherein the control unit is further adapted to select the number of turning points, zero or more, and their positions depending on said external data.

23. An x-ray apparatus according to claim 21, wherein the control unit is further adapted to minimize the number of turning points under the constraint of achieving tomo-angles in the object scan, depending on said external data.

24. An x-ray apparatus according to claim 21, wherein the control unit is adapted to control the movement of the x-ray source and the detector such that when both the x-ray source and the detector move towards their first turning points the x-ray source reaches the first turning point before the detector reaches the first turning point.

25. An x-ray apparatus according to claim 24, wherein the control unit is adapted to control the movement of the x-ray source and the detector such that the x-ray source and the detector changes direction immediately after reaching the first turning point and starts to move in the second direction.

26. An x-ray apparatus according to claim 24, wherein the control unit is adapted to change direction of the x-ray source at a second turning point, wherein the control unit is adapted to control the movement of the x-ray source and the detector such that the x-ray source changes direction and starts to move in the first direction at the second turning point when the detector reaches the first turning point.

27. An x-ray apparatus according to claim 22, wherein one of the x-ray source and the detector stops after reaching the first turning point until the other of the x-ray source and detector reaches the first turning point, whereafter the one of the x-ray source and the detector starts to move in the second direction.

28. An x-ray apparatus according to claim 24, wherein the x-ray source moves with a higher speed than the detector.

29. An x-ray apparatus according to claim 1 wherein the control unit is further adapted to control the movement of the x-ray source and the detector based on positions of the x-ray source and the detector.

30. An x-ray apparatus according to claim 29, wherein the positions are predefined.

31. An x-ray apparatus according to claim 30 wherein the control unit is adapted to control the movement of the x-ray source and the detector such that a speed of the x-ray source is higher than a speed of the detector.

32. An x-ray apparatus according to claim 29, wherein the predefined positions correspond to positions reached during a scan of an object, whereby an area in the object has been identified that requires a specific scan movement, wherein the ratio of the speeds of the x-ray source and the detector increases.

33. An x-ray apparatus according to claim 1, wherein an optimization is performed for maximizing a tomographic angle within a detected object, under a tradeoff of minimizing the movement of the X-ray source.

34. An x-ray apparatus according to claim 30, wherein that a speed of at least the x-ray source decreases as the predefined position of the x-ray source is reached, and the predefined position of the detector is reached.

35. An x-ray apparatus according to claim 34, wherein the x-ray apparatus further comprises a device for taking biopsy samples from a breast as the positions are reached, wherein the positions correspond to positions whereby an area in the object is identified that requires biopsy sampling.

36. An x-ray apparatus according to claim 1, wherein the x-ray apparatus comprises an upper portion and a lower portion, wherein the x-ray source is pivotally arranged in a first end of a first suspension arm, wherein the second end of a first suspension arm being slidingly arranged in a first end of a second suspension arm, wherein a second end of the second suspension arm is pivotally arranged in a lower portion, wherein a first linear screw is arranged in the x-ray portion near the x-ray source to control the movement of the x-ray source in a horizontal direction, a second linear screw is arranged in the lower portion near the detector assembly to control the movement of the detector assembly in a horizontal direction, and a third linear screw is arranged in the second suspension arm to control the movement of the scan arm in a vertical direction.

37. An x-ray apparatus according to claim 36, wherein the first portion of the x-ray apparatus is essentially fixed in space.

38. An x-ray apparatus comprising:
an x-ray source adapted to emit an x-ray beam,
a detector adapted to receive the x-ray beam of the x-ray source,
wherein the x-ray source is able to be moved during at least a scan of an object,
wherein the detector is able to be moved without moving the x-ray source,
the x-ray apparatus further comprising a control unit for controlling the movement of the x-ray source and detector,
wherein further the x-ray beam is directed essentially towards the detector during the movement of the x-ray source and the detector,
wherein the control unit is adapted to receive external data,
wherein the to control unit is further adapted to control paths of movement of the combination of the x-ray source and the detector based on said external data, and
wherein external data comprises data related to the object.

39. An x-ray apparatus according to claim 38, wherein the control unit is adapted to control the movement of the x-ray source along a first movement path and control the movement of the detector along a second movement path respectively during a scan movement, based on the external data.

40. An x-ray apparatus according to claim 38, wherein the external data is received by the control unit during the scan.

41. An x-ray apparatus according to claim 38, wherein the external data is related to a boundary or thickness of the object to be scanned, or a region of interest, wherein said apparatus comprises means for measuring said external data after positioning the object and before finishing the scan.

42. An x-ray apparatus according to claim 39, wherein movement of the x-ray source along the first movement path and the movement of the detector along the second movement path, correspond to a combined movement path, wherein said combined movement path can be represented by a curve through a multi-dimensional parametric space involving a position along one axis and an angle between said x-ray source and detector.

43. An x-ray apparatus according to claim 39, wherein said first movement path and said second movement path is adapted for optimizing local tomographic projection angles and minimizing movements of said x-ray source.

* * * * *